(12) United States Patent
Bennett et al.

(10) Patent No.: US 8,550,477 B2
(45) Date of Patent: Oct. 8, 2013

(54) SPA CART SYSTEM AND METHOD

(76) Inventors: Vickie Bennett, Caledonia, MI (US); Victor Bennett, Caledonia, MI (US)

( * ) Notice: Subject to any disclaimer, the term of this patent is extended or adjusted under 35 U.S.C. 154(b) by 474 days.

(21) Appl. No.: 12/777,581

(22) Filed: May 11, 2010

(65) Prior Publication Data

US 2010/0289236 A1 Nov. 18, 2010

Related U.S. Application Data

(60) Provisional application No. 61/178,223, filed on May 14, 2009.

(51) Int. Cl.
- *B62B 3/00* (2006.01)
- *B62B 3/02* (2006.01)
- *B62B 3/04* (2006.01)
- *B62B 3/10* (2006.01)

(52) U.S. Cl.
USPC ............... 280/47.35; 280/47.34; 280/79.11; 280/79.3

(58) Field of Classification Search
USPC ................. 280/47.34, 47.35, 47.36, 47.371, 280/79.11, 79.2, 79.3, 79.9
See application file for complete search history.

(56) References Cited

U.S. PATENT DOCUMENTS

| | | | | |
|---|---|---|---|---|
| 2,819,938 | A * | 1/1958 | Zerver | 312/201 |
| 3,031,084 | A * | 4/1962 | Mugler | 108/16 |
| 3,874,531 | A * | 4/1975 | Mayo | 414/680 |
| 3,957,038 | A | 5/1976 | Roberts | |
| 4,305,171 | A * | 12/1981 | Pettersson | 114/343 |
| 4,782,873 | A * | 11/1988 | Messner et al. | 150/154 |
| 4,976,450 | A * | 12/1990 | Ellefson | 280/79.11 |
| 5,083,241 | A * | 1/1992 | Foster | 362/33 |
| D403,772 | S | 1/1999 | Fanuzzi | |
| 6,217,045 | B1 | 4/2001 | Leyton | |
| 6,615,431 | B2 * | 9/2003 | Lin | 5/620 |
| 6,820,878 | B2 * | 11/2004 | Safari et al. | 280/47.26 |
| 7,213,817 | B2 * | 5/2007 | Cheung | 280/42 |
| 7,316,657 | B2 | 1/2008 | Kleinhenz et al. | |
| 7,475,439 | B1 | 1/2009 | Cox et al. | |
| 7,487,818 | B2 * | 2/2009 | Zimmer | 160/348 |
| 7,610,863 | B1 | 11/2009 | Smith-Huebner | |
| 7,661,459 | B2 | 2/2010 | Wesley et al. | |
| 2003/0032901 | A1 | 2/2003 | Webb | |
| 2005/0242534 | A1* | 11/2005 | Woods et al. | 280/47.34 |
| 2006/0097489 | A1* | 5/2006 | Cheung | 280/651 |
| 2009/0166991 | A1* | 7/2009 | Cai | 280/47.35 |

* cited by examiner

*Primary Examiner* — Hau Phan
*Assistant Examiner* — Bryan Evans
(74) *Attorney, Agent, or Firm* — Price Heneveld LLP

(57) ABSTRACT

A spa cart system includes a wheeled cart with multiple shelves for carrying spa products and fully-functional equipment for providing spa services in a client's room or designated hotel site, such as a full body massage, manicure, pedicure, and many more. Selectable transportable modules include products and equipment to support a variety of diverse spa activities, such as carrying necessary equipment, including electrically-powered equipment and a massage table and positioning same for use, supporting portability such as a cart width that fits through typical narrow hotel and resort doors, allowing adjustable movement of the equipment to use locations, providing a well-organized physical station supporting the various services (e.g., a manicure treatment station), and providing modules selectable by the technician to satisfy various spa activities pre-selected by a client.

20 Claims, 20 Drawing Sheets

SPA CART SYSTEM AND METHOD

This application claims benefit under 35 USC section 119(e) of provisional application Ser. No. 61/178,223, filed May 14, 2009, entitled SUITE SPA CART SYSTEM, the entire contents of which are incorporated herein by reference.

BACKGROUND

The present invention relates to carts equipped to perform spa services, and more particularly relates to a cart system having multiple functional components and products thereon facilitating a full spa experience, yet that is portable, well-organized, flexible-in-use, and multifunctional while maintaining ease of use and aesthetics for each spa experience selected. The present invention further includes a spa cart system with modules selectable to facilitate particular spa activities.

Many hotels, resorts, retirement homes, etc. want to offer spa services to clientele, but cannot due to space constraints, capital-investment, logistics, and other considerations. This is unfortunate, since spa services are in high demand, especially at luxurious hotels and resorts. Not only does this result in clients going elsewhere to receive the services, but also the clients can be frustrated because of this inconvenience. As a practical matter, this also results in a lost opportunity for the hotels/resorts to earn supplementary income. In fact, some business is likely lost directly due to lack of a spa facility.

Notably, spa services require a high level of excellence and quality in order to match the sophistication and décor of the hotel offering the services. In other words, a poor spa experience can lead to customer dissatisfaction and ultimately an overall net loss of business. Further, there may be health and sanitary issues where hot moist treatments are provided.

Still further, spa services include a wide range of products (such as oils, nail polishes, makeup, and the like) and require a variety of different support components (such as a massage table, a shelf for manicures, a steamer for moisture treatments, heated stones, a foot pan for pedicures, a heater, a tanning light, a microdermabrasion treatment unit, a heater for products applied hot, and the like). It is very difficult to support all of these different products and components in a well-organized manner that meets both functional accessibility and aesthetics required for providing such services.

SUMMARY OF THE PRESENT INVENTION

In one aspect of the present invention, a spa cart system includes a wheeled spa cart with at least one component configured to support at least one spa service selected from a group of spa services including a back massage, a body massage, a facial, stone therapy, manicure, pedicure, microdermabrasion treatment, paraffin treatment, tanning, and a spa therapy activity using hot moist towels, and also including a massage bed releasably secured to a side of the wheeled spa cart.

In another aspect of the present invention, a spa cart system includes a wheeled spa cart with corner posts and multiple extendable shelves supported by glides on the corner posts and having at least two open sides for accessing the shelves, and at least one flexible sheet wrap covering the open sides and releasably attached to the corner posts, whereby stored product is accessible from the open sides.

In another aspect of the present invention, a spa cart system includes a wheeled spa cart with corner posts, a functional spa component, and a cantilevered arm engaging a top of one of the corner posts and supporting the functional component for movement between storage position generally above the spa cart and a use position generally outside a periphery of the spa cart.

In another aspect of the present invention, a spa cart system includes a wheeled spa cart with corner posts, a manicure table supported on glides for double-length extension, and storage bins adapted to support manicure products for display and for access to a technician sitting at the manicure table and servicing a client.

In another aspect of the present invention, a spa cart system includes a wheeled spa cart with corner posts and at least one extendable shelf, and a plurality of at least three different modules each configured for supporting different spa activities, and the at least one extendable shelf having sufficient room to support at least two of the different modules.

The present invention also includes methods related to the above concepts.

The present invention also includes a new, ornamental, and unobvious appearing cart, by itself and/or with the massage table.

These and other aspects, objects, and features of the present invention will be understood and appreciated by those skilled in the art upon studying the following specification, claims, and appended drawings.

DETAILED DESCRIPTION OF PREFERRED EMBODIMENTS

Figure 1:
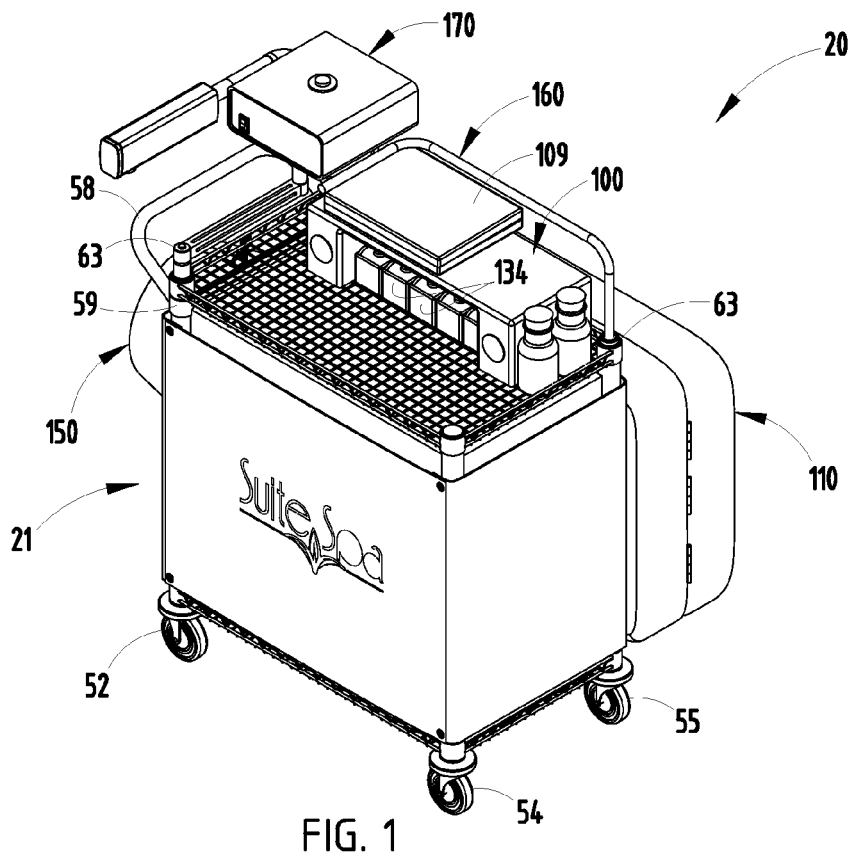
FIGS. 1-4 are perspective assembled views, taken from all corners, of the present spa cart system in a storage position.
Figure 2:
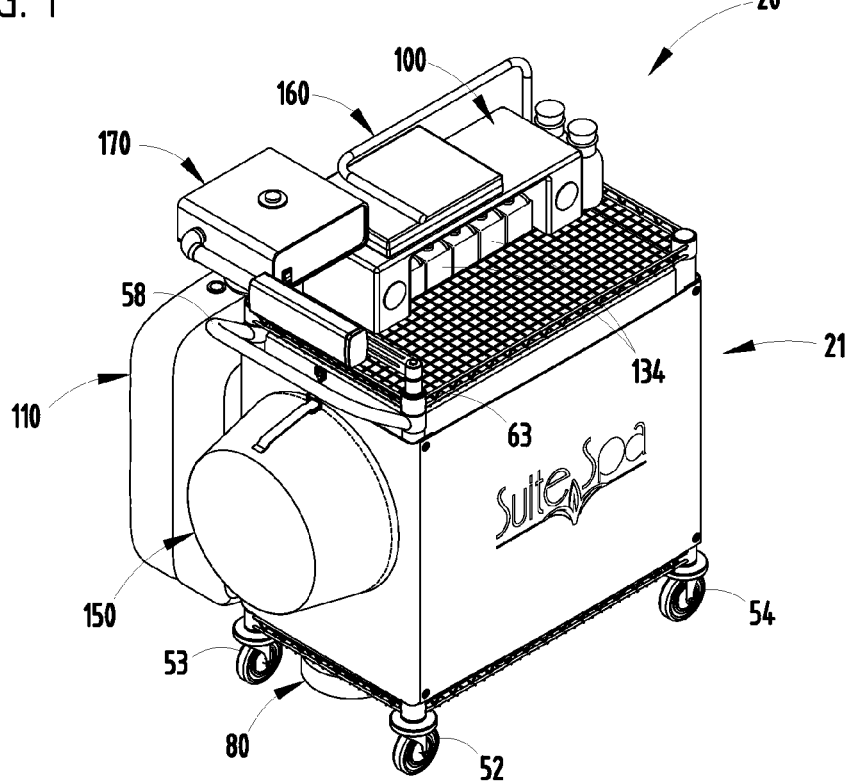
Figure 3:
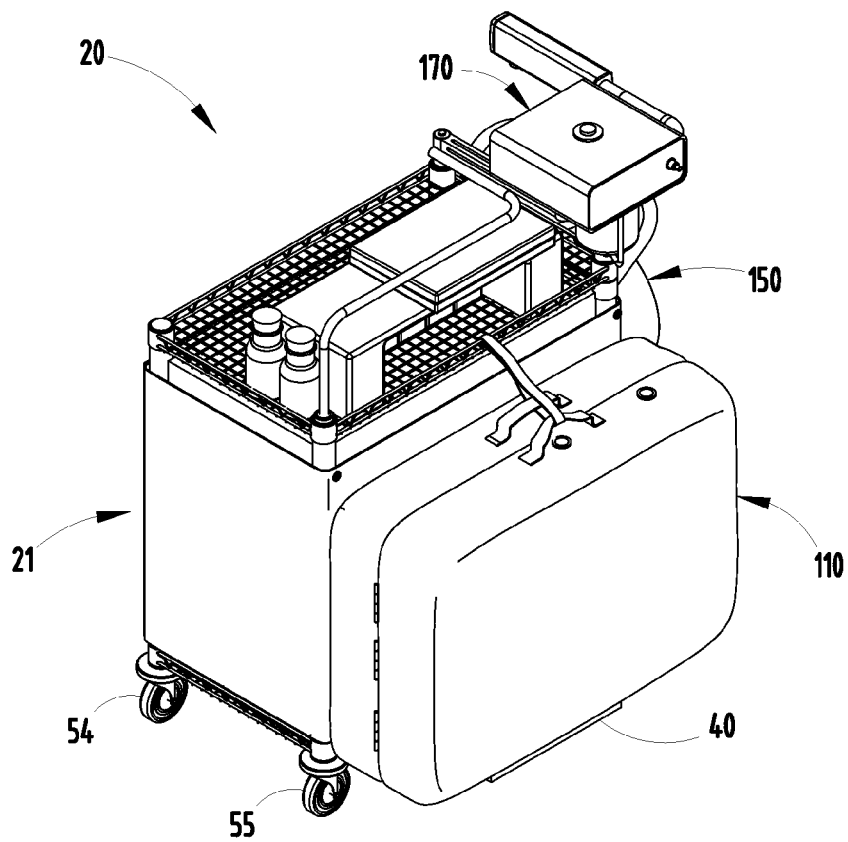
Figure 4:
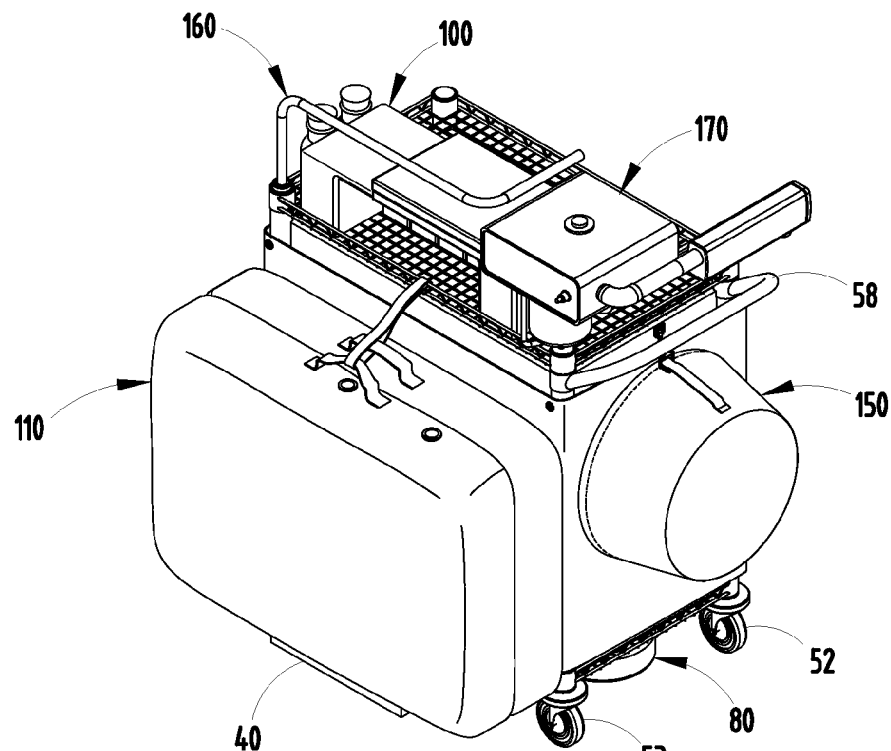

The present spa cart system 20 (FIGS. 1-2) (called a "Suite Spa Cart") includes a steerable wheeled cart 21 with multiple shelves and storage capacity particularly constructed to provide portable, fully-functional equipment for providing spa services, including but not limited to: a full body massage with background music, manicure, pedicure, facial hot stone therapy, herbal body wrap, mud wrap, paraffin treatment, aroma therapy, infrared sauna, and/or microdermabrasion treatment, tanning, and related spa activities. The system 20 includes features on the cart that 1) carry necessary equipment, including electrically-powered equipment, 2) allow portability such as a width less than 30 inches (or more preferably less than about 29 inches even when a massage table is attached to the cart) so that the cart fits through typical narrow hotel and resort doors; 3) when at the site of service, allow adjustable movement of the equipment to points of use (such as adjacent the cart but outside a periphery of the cart), 4) provide a well-organized physical station for supporting the various services (such as a manicure treatment station), including relatively easy access to necessary products, and 5) modules selectable by the technician to satisfy various spa activities pre-selected by a client.

Figure 5:
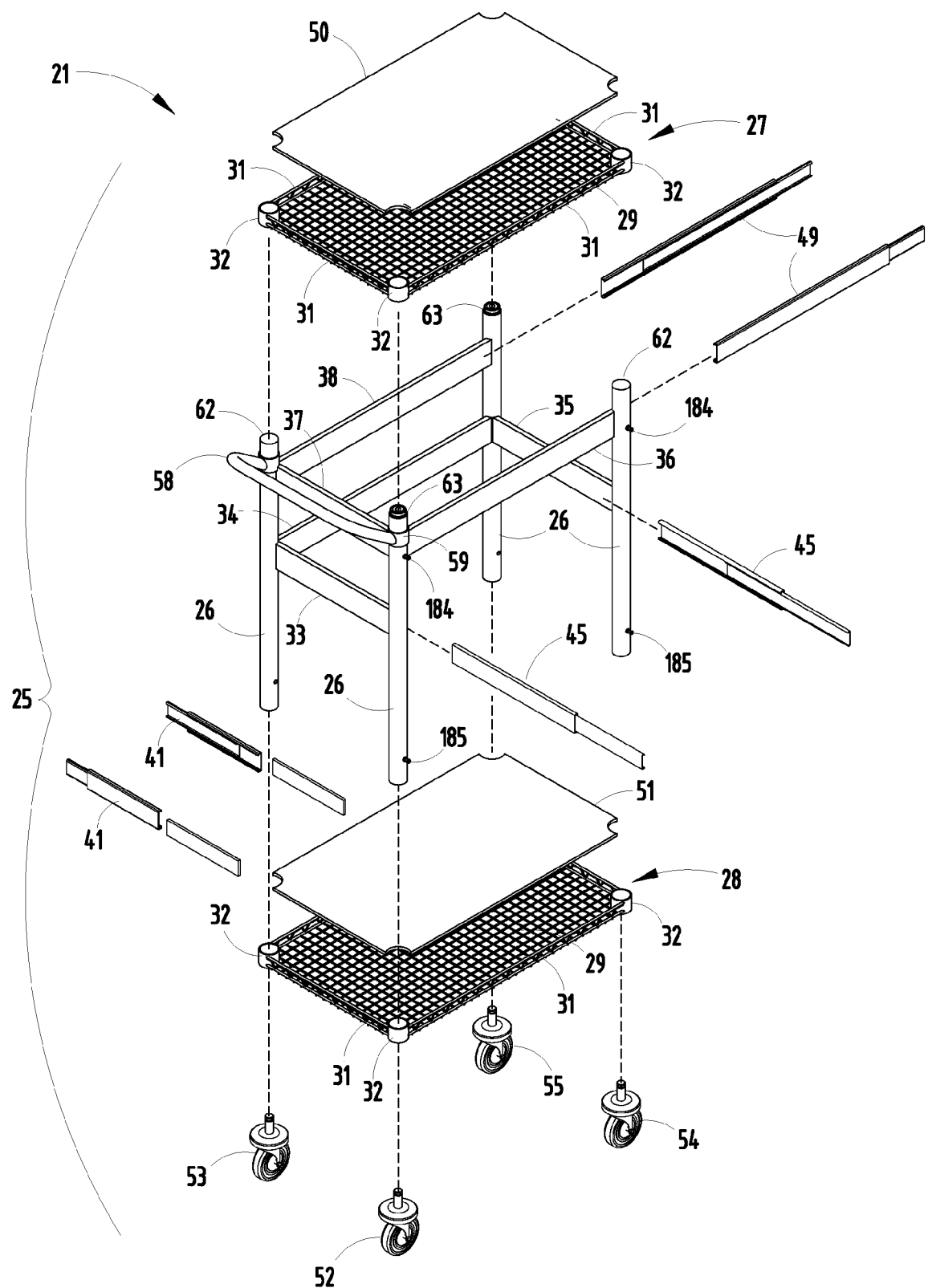
FIG. 5 is an exploded perspective view of the cart frame and shelf glides.
Figure 6:
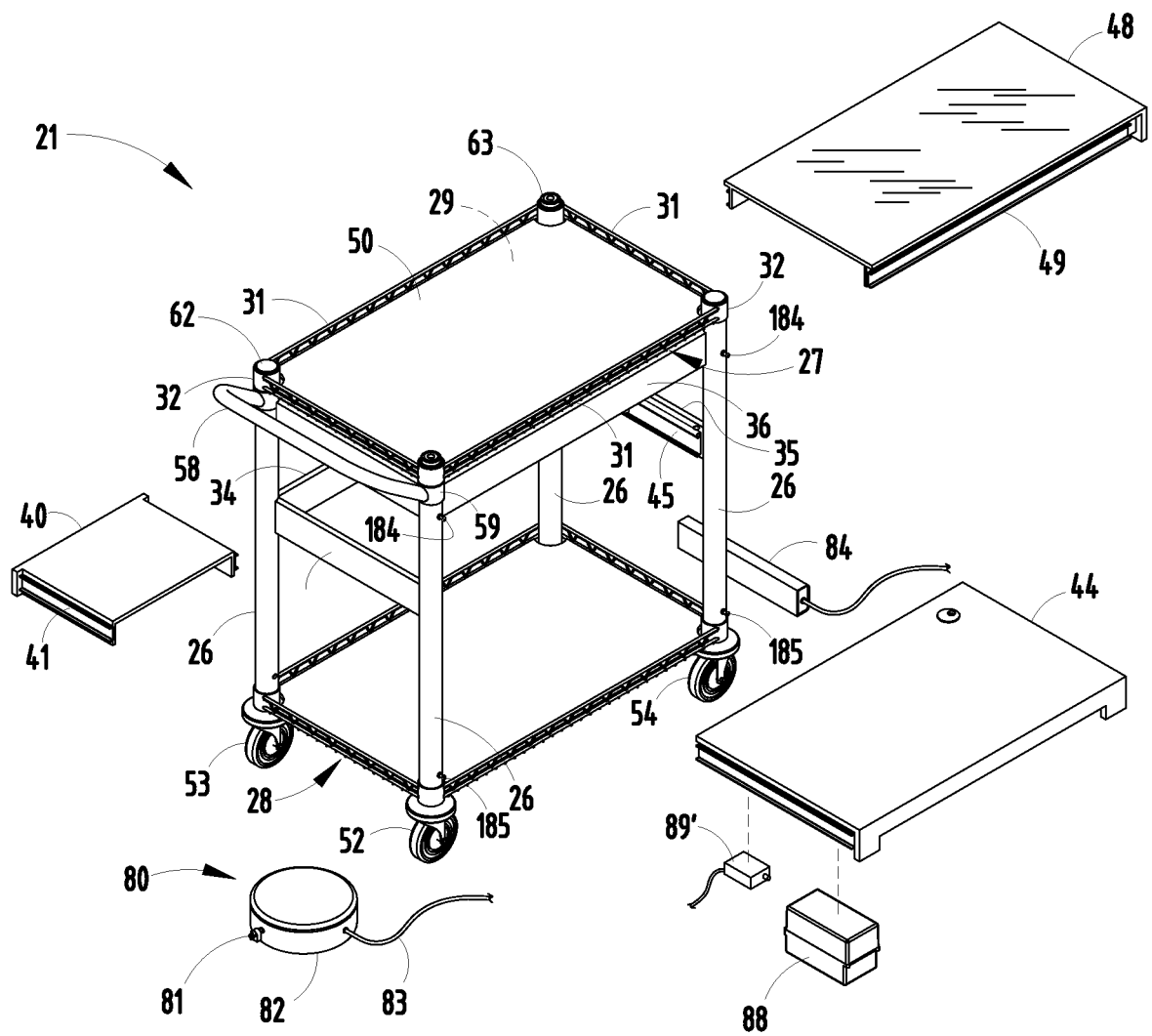
FIG. 6 is a perspective view of the spa cart frame of FIG. 5, including three shelves, cord reel, and electrical components.

The cart system 20 (FIGS. 1-2) includes a cart 21 with cart frame 25 (FIG. 5) made of corner posts 26 and high/low wire mesh post-engaging panel supports 27 and 28. Each panel support 27/28 includes a wire mesh panel 29 (which could be other than wire mesh), edge beams 31 and post-engaging tube sections 32. Post-to-post beam supports 33-35 and 36-38 are attached between the posts 26 for supporting drawer glides. A retractable/extendable massage table carrier shelf 40 (FIG. 6) (also called a "support") includes glides 41 attached under the low panel support 28. The carrier shelf 40 is positioned at a low height to support a weight of the massage table 110 (FIG. 21) but so that a top of the massage table 110 is generally adjacent the top of the cart 21. Thus, a weight of the table 110 is primarily supported by the shelf 40 but the table can be retained to the cart by holding its handles against the cart by a retainer strap that grips handles on the table 110, as explained below.

A hot tray shelf/drawer 44 (FIG. 6) includes glides 45 attached to beam supports 33 and 35 for pullout/extension from a side of the cart 21 opposite the table carrier shelf 40. The manicure table/double-extend shelf 48 includes glides 49 attached to beam supports 36 and 38 for pullout/extension from an end of the cart 21 opposite the handle 58. A tempered glass shelf panel (FIG. 5) is placed on top of shelf 48, covering the shelf 48 with an aesthetic and chemical resistant surface. Notably, only the illustrated shelf 48 is covered in tempered glass, and the other shelves 50, 51 are leather, vinyl cloth, colored panel, or the like. The cart 21 includes lockable/steerable rubber castors 52-53 at its end adjacent the handle 58, and fixed-axle non-steerable rubber castors 54-55 (lockable if desired). The handle 58 is U-shaped and includes ends mounted on two corner posts 26. The illustrated handle 58 is U-shaped, bent from a tube, and includes a pair of tube sections that slide onto a top of the posts 26 and then are set in place by a set screw (or by welding or other securement means). Specifically, the push handle 58 includes tube sections 59 engaging the two corner posts 26. Post caps 62 engage a top end of the posts 26, or alternatively, a top-of-post socket connector 63 with socket 64 engages a top end of the posts 26 where a functional spa component will be supported by a cantilevered arm, such as a steamer or light. Electrical grommets (such as rubber grommets) fit into holes in the tubular posts 26 to facilitate routing wiring into (or from) the tubular posts 26 without fear of cutting insulation on the wiring and short-circuiting the electrical power. It is noted that electricity can be routed throughout the cart and interconnected to the various functional components by different means. For example, all wiring could be pre-routed and permanently connected to known functional components on the cart. However, by providing extension cords that extend through the corner posts 26 from the surge protector 84 to the level of usage on the cart 21, electrical plugs can be made available at an appropriate height and corner locations on the cart for plugged-in connection by the electrical cords of the various spa-supporting components. This allows the technician to select different electrically-operated functional components for different clients, depending on their preselected desired spa treatments. Alternatively, the electrical cords of the spa-supporting components themselves can be routed through holes/grommets downwardly through the corner posts 26 to be plugged into one of the multiple outlet ports of the surge protector 84.

The wiring can be conveniently conveyed around the cart 21 by various means, such as routing the wiring through the inside of the posts, or along an outside of the posts (covered by an aesthetic cover), and in other ways. In the illustrated cart 21, electrical current is communicated from a room-electrical outlet through cord 81 to reel 82, through wire 83 to surge protector 84, then through additional wires extending up thru each corner post 26. For maximum flexibility, the wires extending upward through the posts 26 can be extension cords attached to the various spa electrical components, which are plugged into one of the cords as needed. Alternatively, a wiring harness can be used to minimize cost and installation space.

Figure 7:
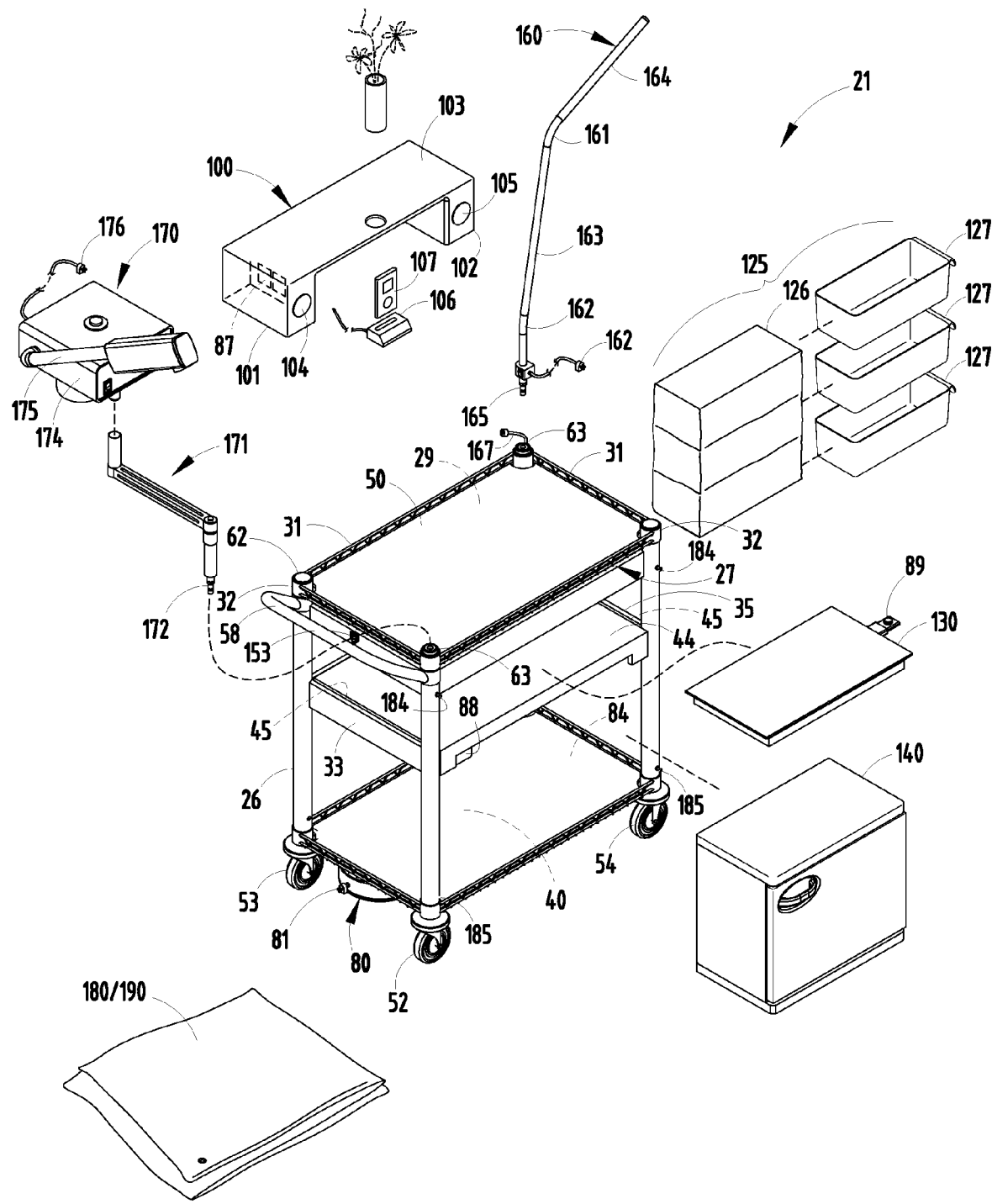
FIG. 7 is a perspective view showing the spa cart of FIG. 6 assembled, and with various spa-supporting components, including the transaction counter with integral speakers and wiring, the steamer with cantilevered multi-bend arm support, the bendable adjustable post light, the hot plate with heat controls, the hot towel caddie, the flexible three-drawer/tub storage and three tubes, and the cover wrap (removed and folded).

The illustrated cart 21 includes an electrical system 80 having an extension cord 81 wound on a spring-biased reel 82. The cord 81 can be pulled to extend the cord 81 to a room electrical outlet so that 120 VAC electrical power (or other electrical power, depending on the country of use) can be supplied to the cart system 20. Wires 83 extend from the reel 82 to a 5-outlet surge protector 84 attached under the lower panel support 28. Hard-wired power supply wires 85 extend from the surge protector 84 (or are spliced into the reel 82) and are routed to the music station 86 for the iPod docking station and/or to a computer plug-in outlet 87 on the transaction shelf. A transformer 88 can be incorporated into the circuitry so that the power supplied is of a desired voltage, amperage, and with sufficient fusing. A switch 89 (FIG. 7) is incorporated into the cart's electrical circuit for powering the hot plate 130 on the hot drawer 44, and includes at least two settings, one being an auto-power-on when the drawer is extended, and the other being an absolute-power-on (regardless of whether the drawing is extended or retracted/stored. A proximity switch 89' (FIG. 6) is located to selectively cut power to the hot plate when the hot drawer 44 is closed/stored.

The transaction counter/shelf 100 includes chambered counter side supports 101 and 102, and further includes a transaction shelf/countertop 103 extending between the supported 101 and 102. The shelf 103 covers about half of the top of the spa cart so that product can be displayed on the remainder of the top. The speakers 104 and 105 are positioned in the side supports 101 and 102. An iPod docking station 106 is provided for an iPod 107 loaded with music. Wires extend between the speakers 104/105 and the docking station 106 for communicating electrical signals for generating sound. An outlet 87 is provided under the shelf 103 for supporting the computer 109. It is noted that alternative music-generating systems can be used. For example, the computer 109 could also have music filed in it, and be operably connected to the speakers 104,105.

Figure 21:
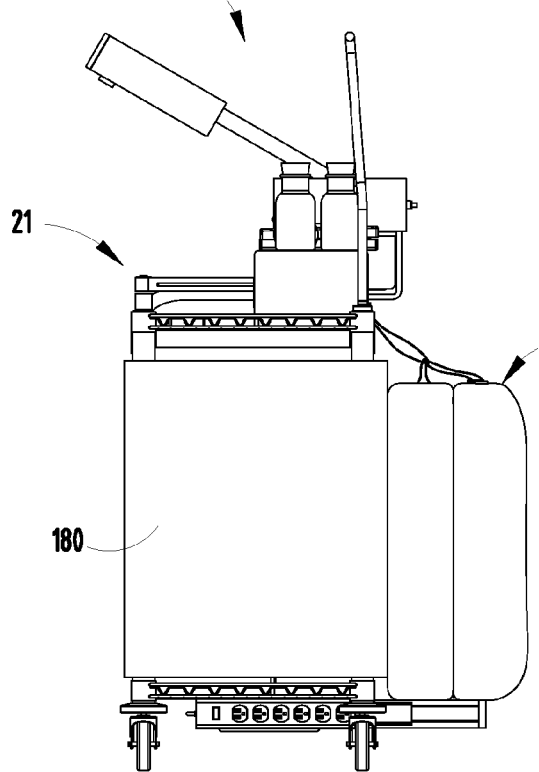
Figure 22:
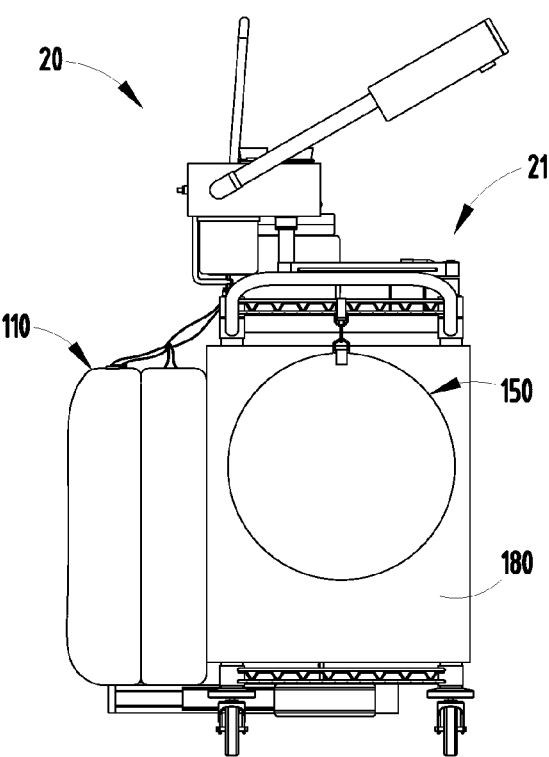
Figure 23:
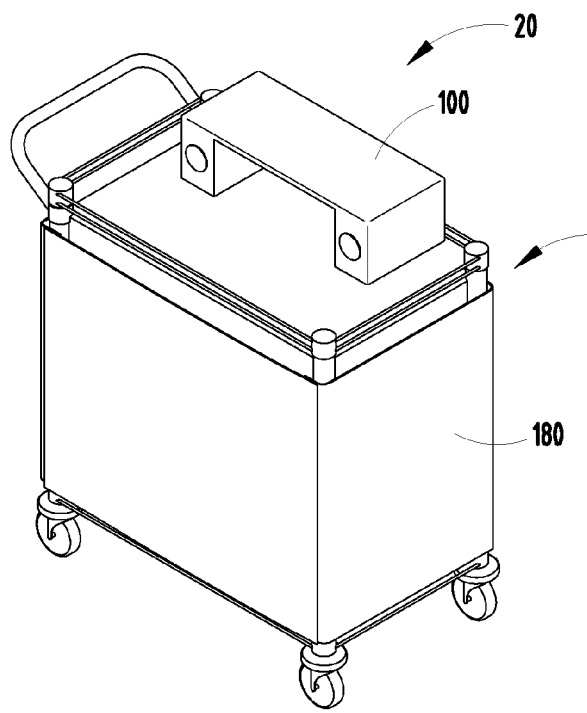
FIGS. 23-26 are perspective, side, rear and front views of the present cart without products thereon and with the massage table removed but showing the transaction counter.
Figure 24:
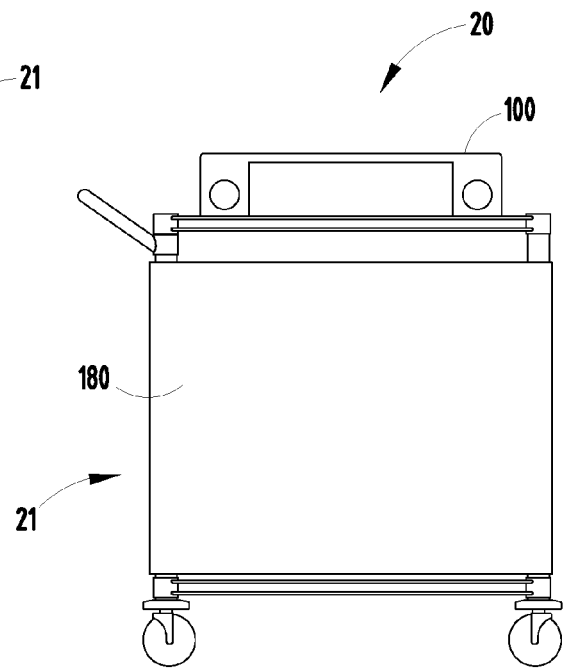
Figure 25:
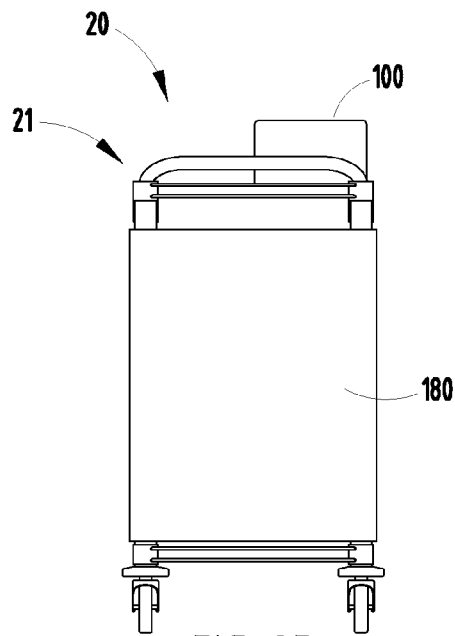
Figure 26:
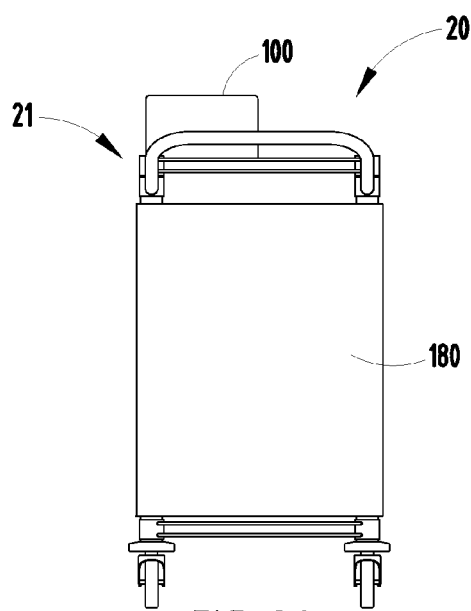
Figure 27:
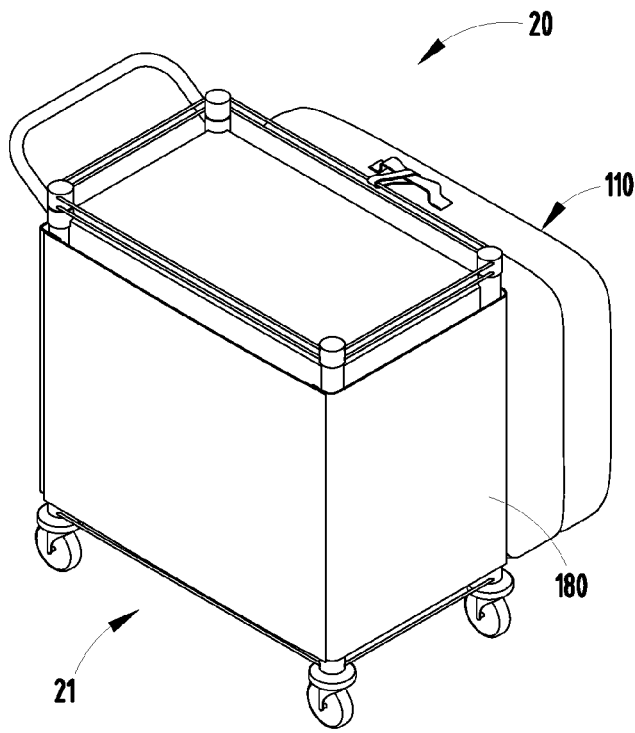
FIGS. 27-31 are perspective, side, opposite side, rear and front views of the present cart without products and without the transaction counter but with the massage table.
Figure 28:
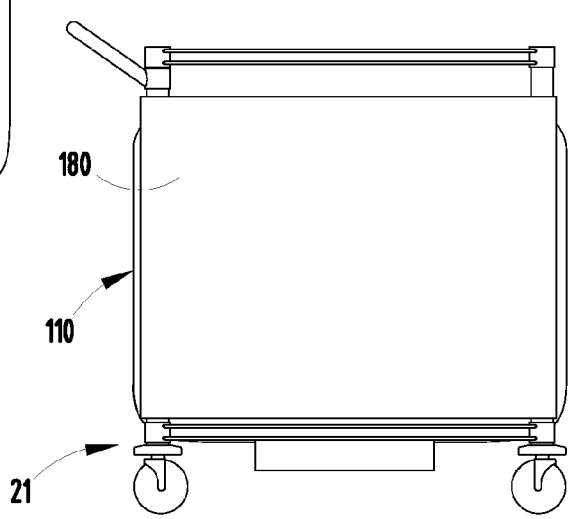
Figure 29:
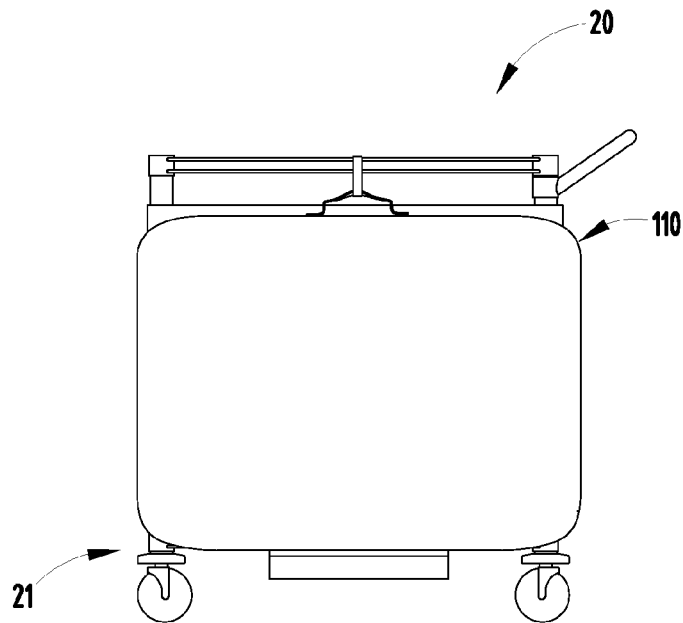
Figure 30:
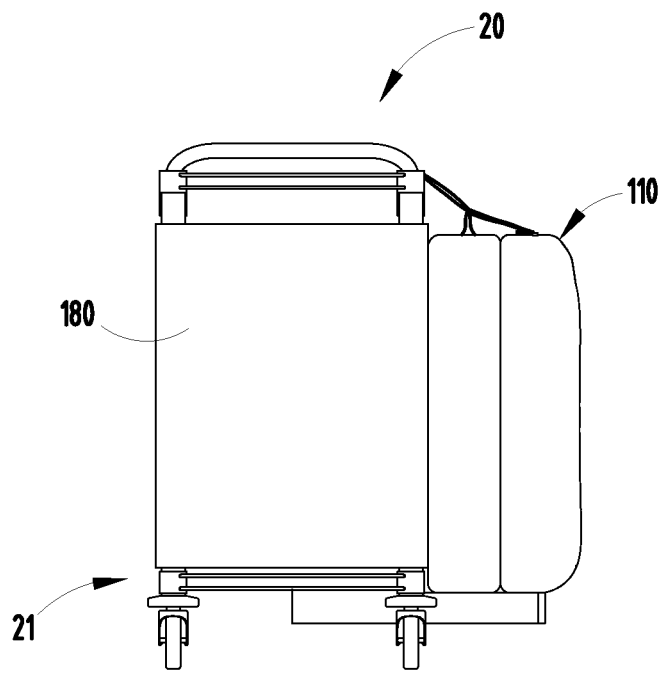
Figure 31:
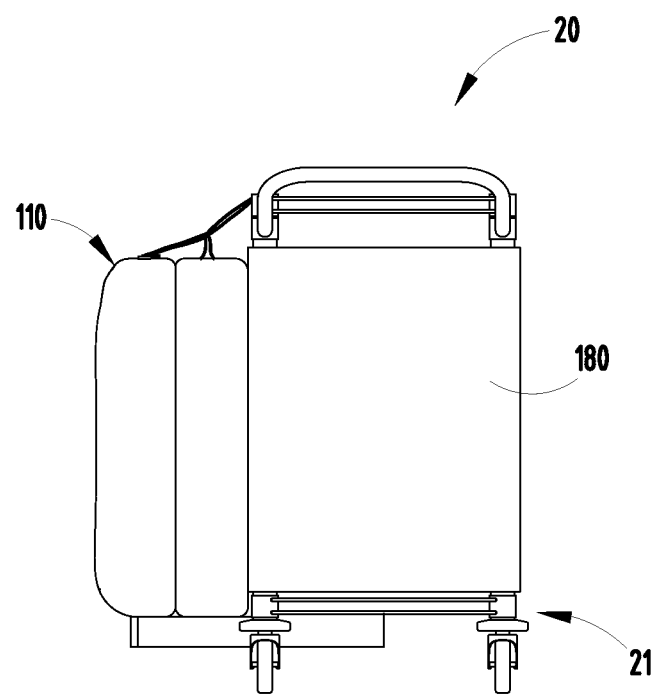

The massage table 110 (also called a "massage bed" herein) includes bi-folding panel frame 111 hinged together and supporting cushions 112. Legs 113 are pivoted to the panel frame 111 and stabilizer cords 114 and braces are provided as needed to stabilize them when the table is erected. The massage table 110 also includes under-bed stored accessories 116 for comfortably supporting a client's head. The massage table 110 is supported on the cart by a massage pullout carrier shelf 40 and glides 41. The massage table 110 includes handles 120, 121 (FIG. 21). A Velcro® strap 122 on the cart 21 is configured to wrap around the handles 120/121 and can be secured as a loop to hold the table 110 on a side of cart 21 (and on the bottom support shelf 40).

Figure 18:
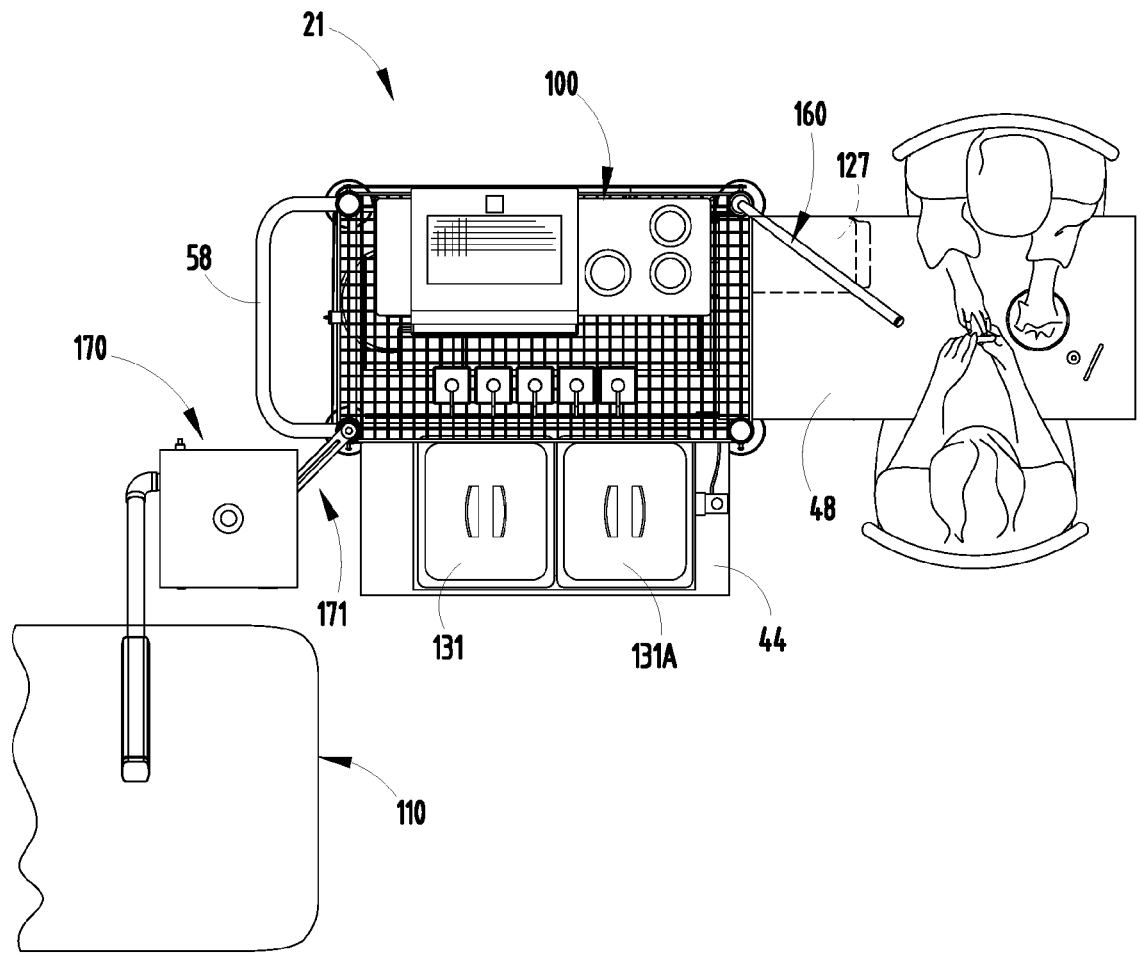
FIG. 18 is perspective view showing the spa cart opened and ready for use, the client receiving a manicure.
Figure 19:
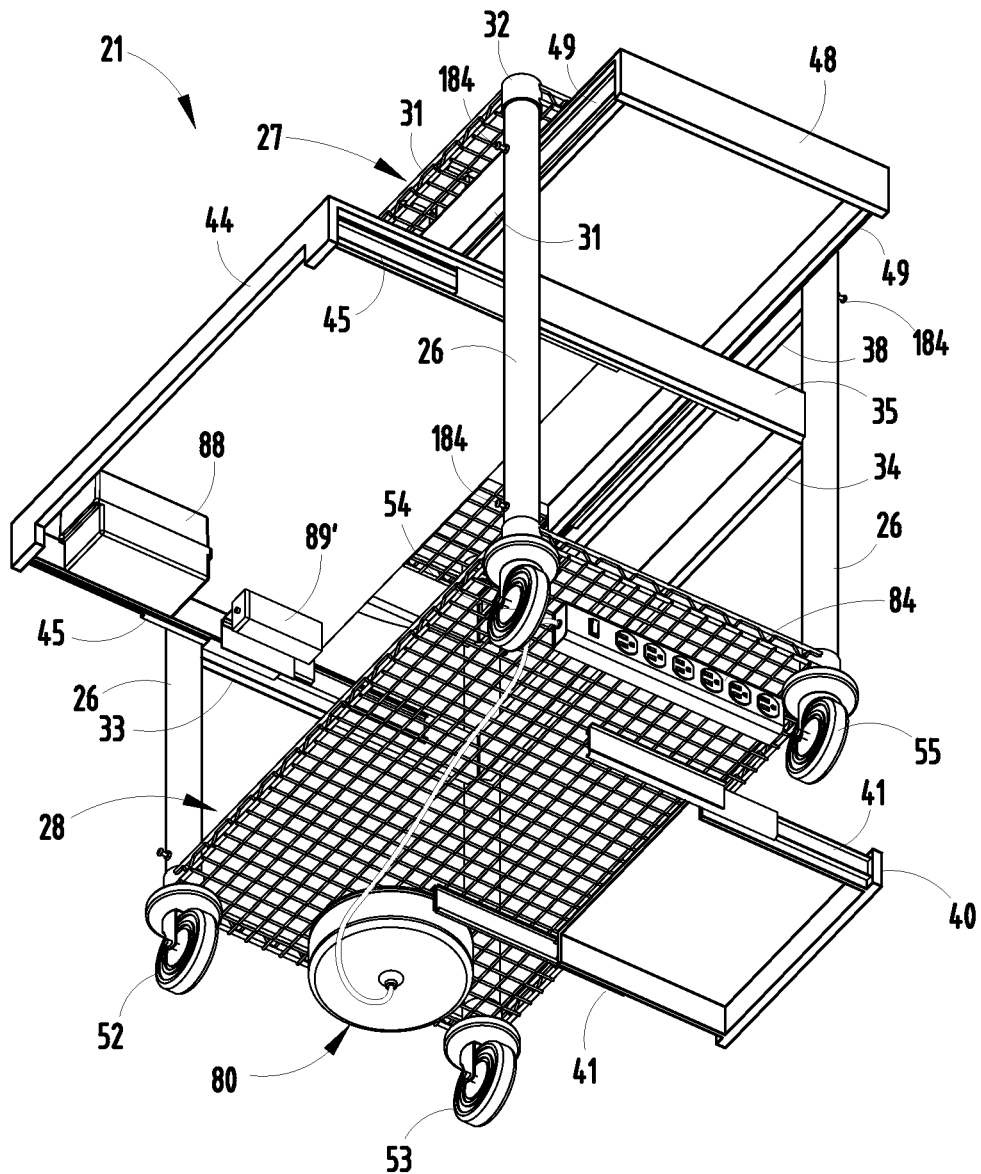
FIG. 19 is a bottom perspective view showing the cart and electrical components thereon.
Figure 20:
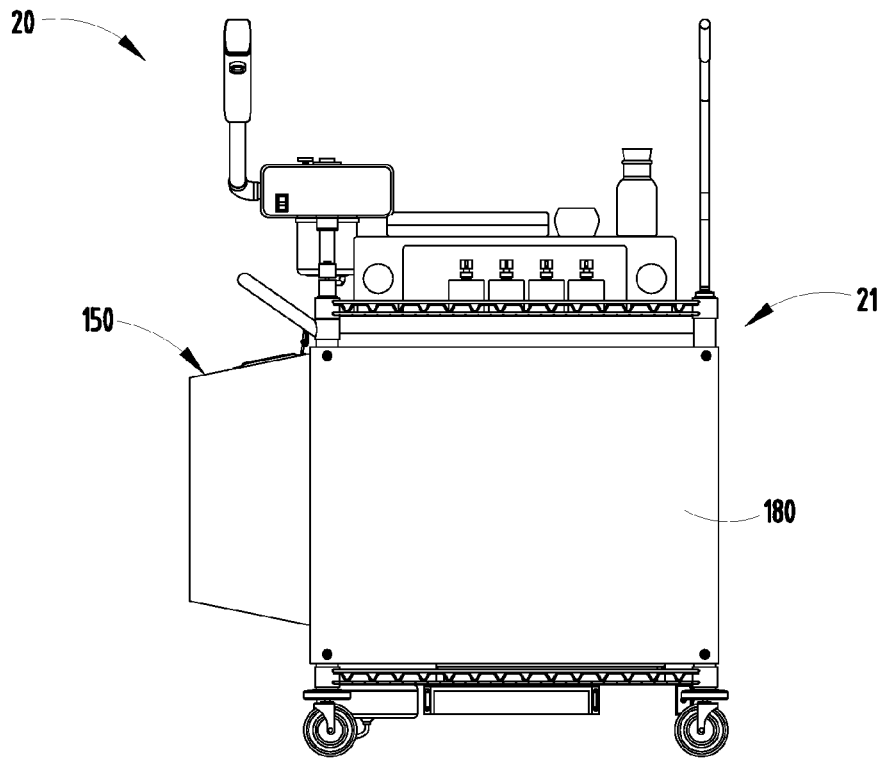
FIGS. 20-22 are side and opposite end views of the spa cart in FIGS. 1-4, showing an appearance of the spa cart.

The manicure table/shelf (FIGS. 6 and 18) 48 comprises a double-length extendable shelf 48 on glides 49. As noted above, it may include a tempered glass top panel so that fingernail polish removers do not mar or damage a finish of the shelf 48. The shelf 48 is supported by double-length extension glides 41, and includes dimensions about equal to the width and length of the cart 21. The shelf 48 can include an edge lip if desired to hold product on the shelf, and can also include a hotel insignia for aesthetics.

A three-tub drawer unit 125 (FIG. 7) includes a flexible outer case 126 and three see-thru tubs 127 that can be removed from it. The drawer unit 125 fits behind the hot towel cabbie 140 on the lower support/shelf 28 in a location easy to reach by a technician when sitting at the manicure shelf 48 and working with a client. There are several excellent product storage areas, such as area 128 to the left of the cabbie 140 that are within easy reach of the working technician.

Figure 8:
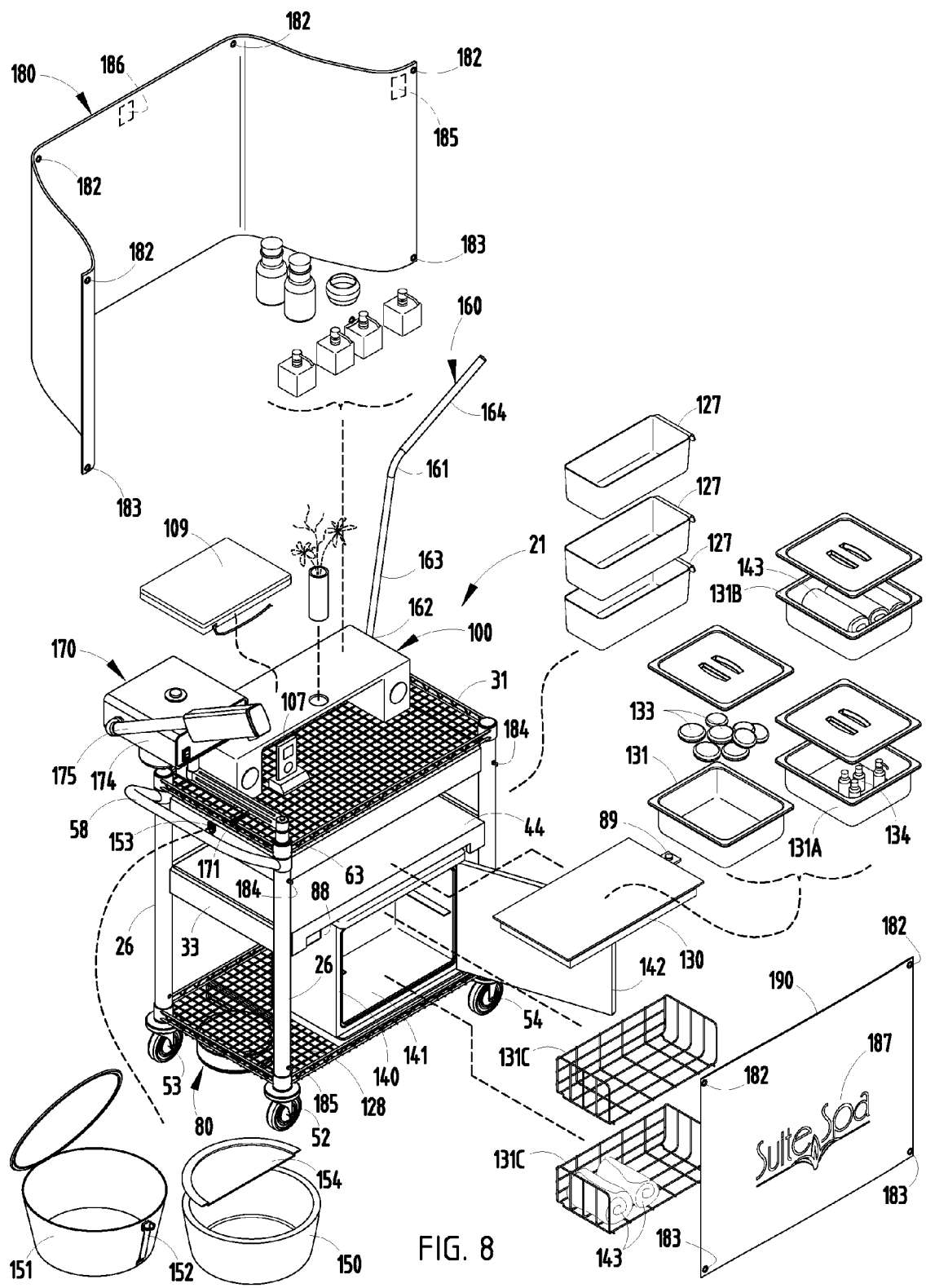
FIGS. 8-9 are exploded perspective views of the spa cart with various products and modules shown and potential placement locations of same on the cart.
Figure 9:
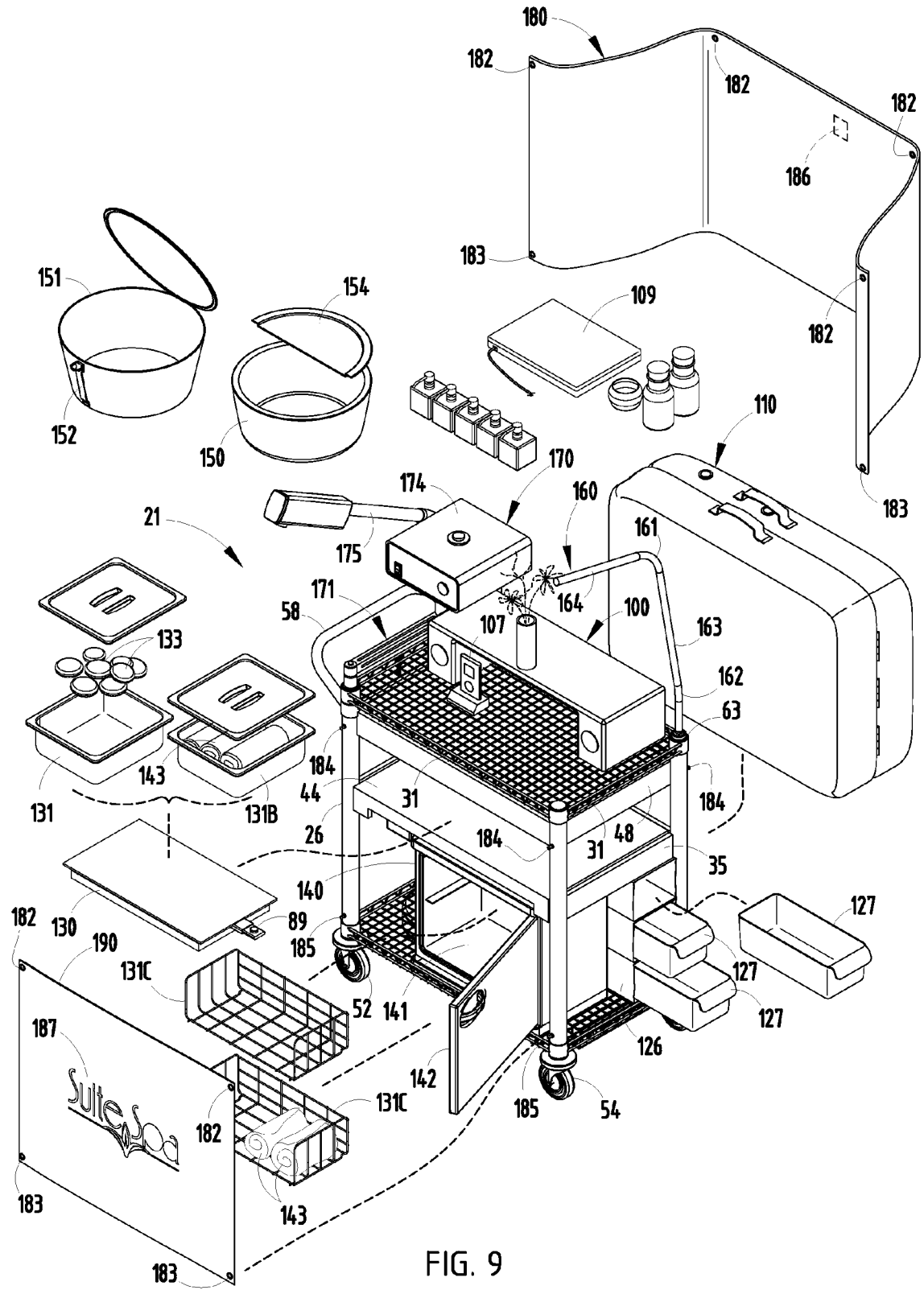
Figure 10:
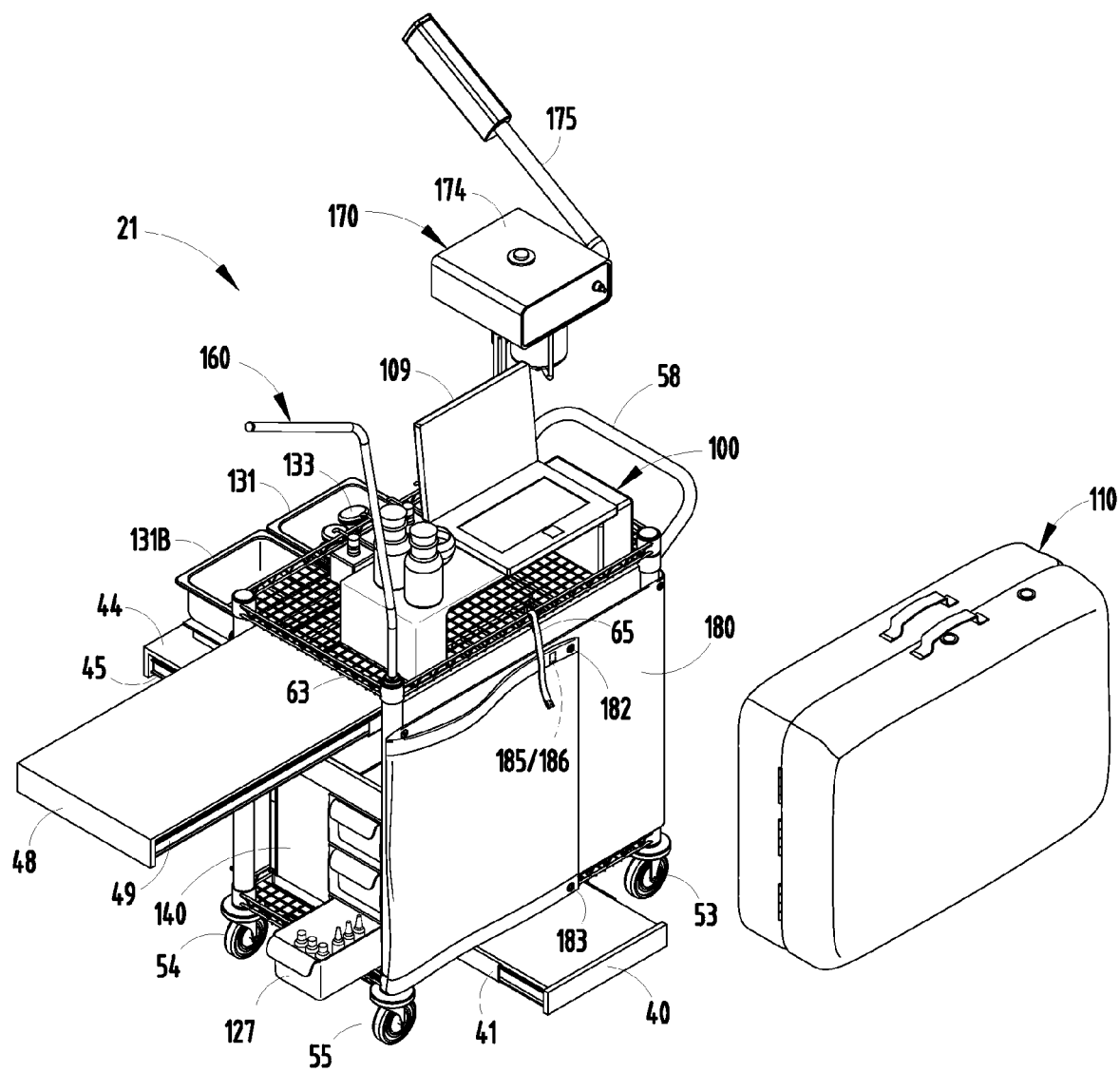
FIG. 10 is a perspective view showing the massage table removed but with the lower support still extended, and also showing the manicure shelf extended as well as a product tub pulled partially out, and also the wrap held in a flap-open position.
Figure 11:
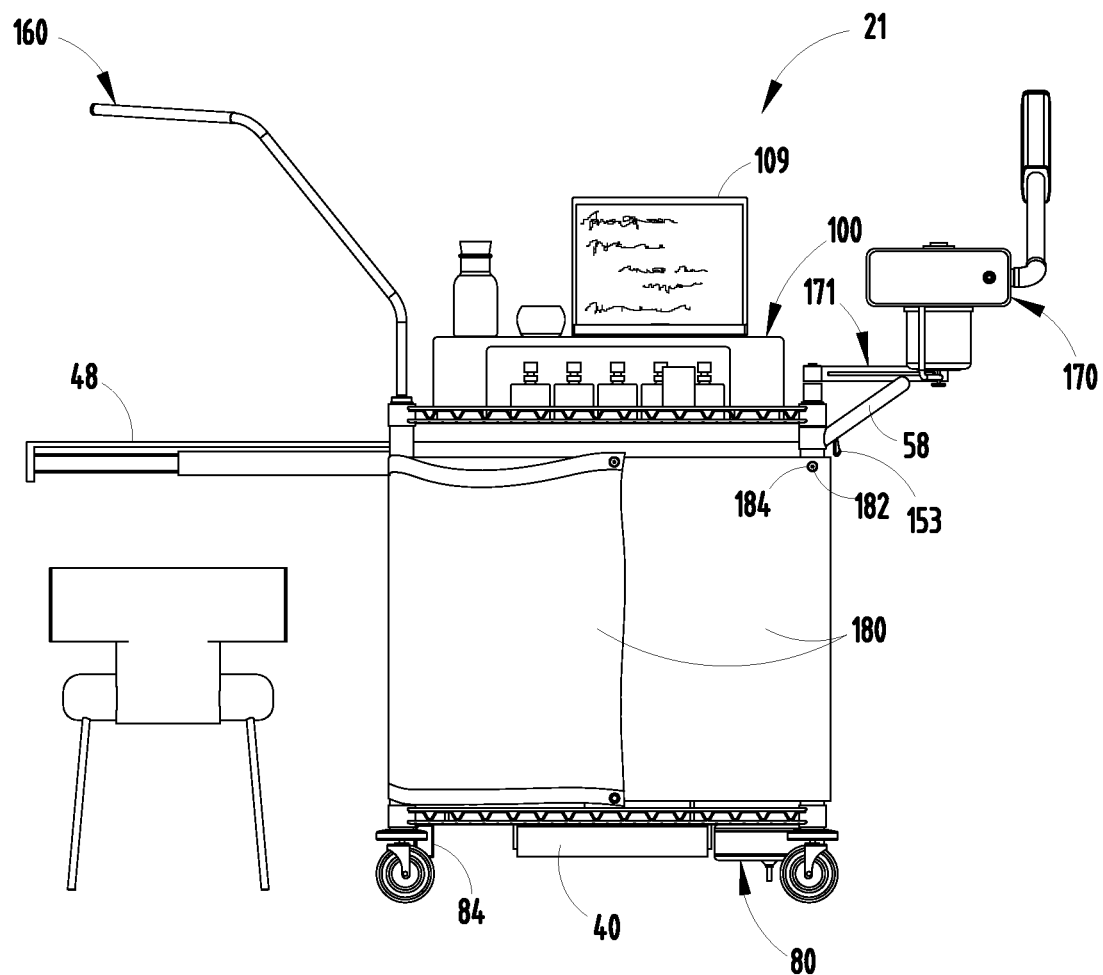
FIGS. 11-14 are elevational views of opposite sides and ends of the spa cart of FIG. 10.
Figure 12:
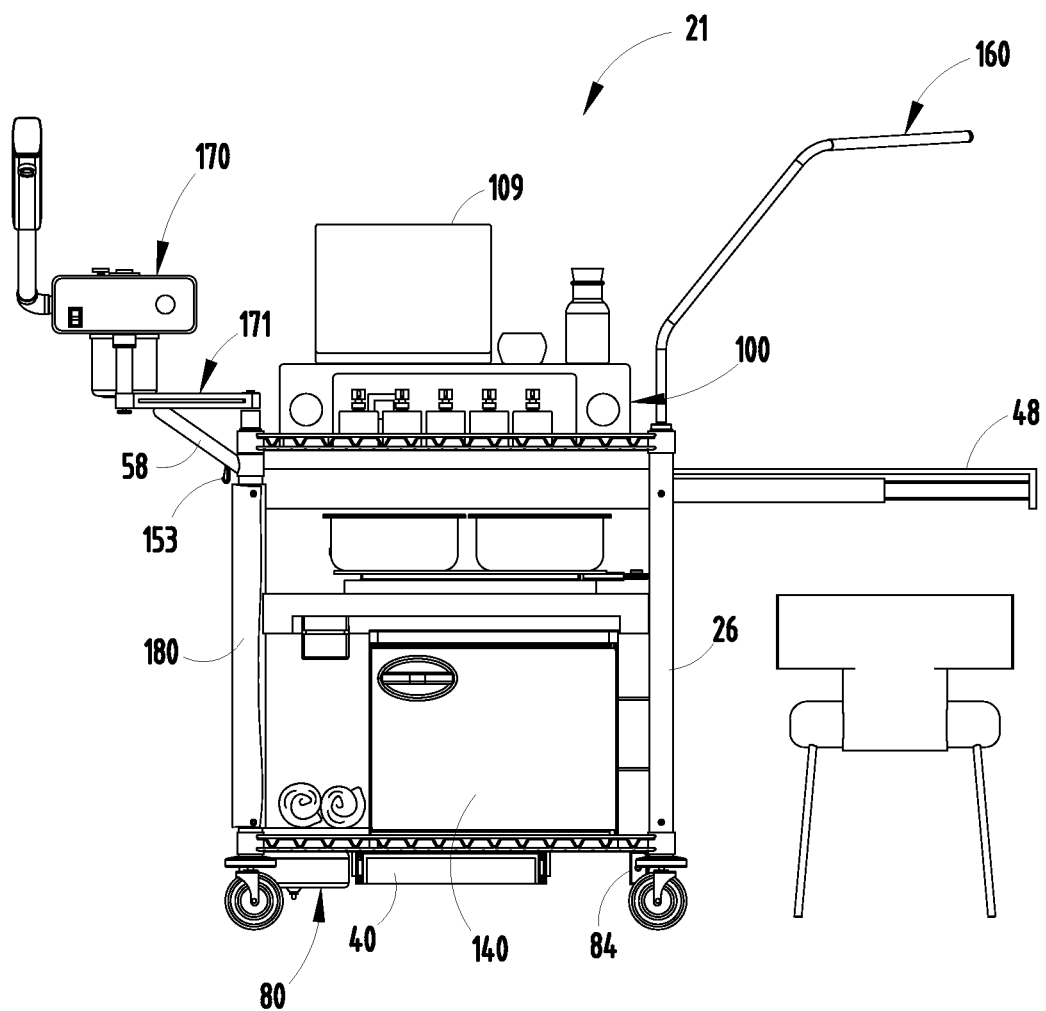
Figure 13:
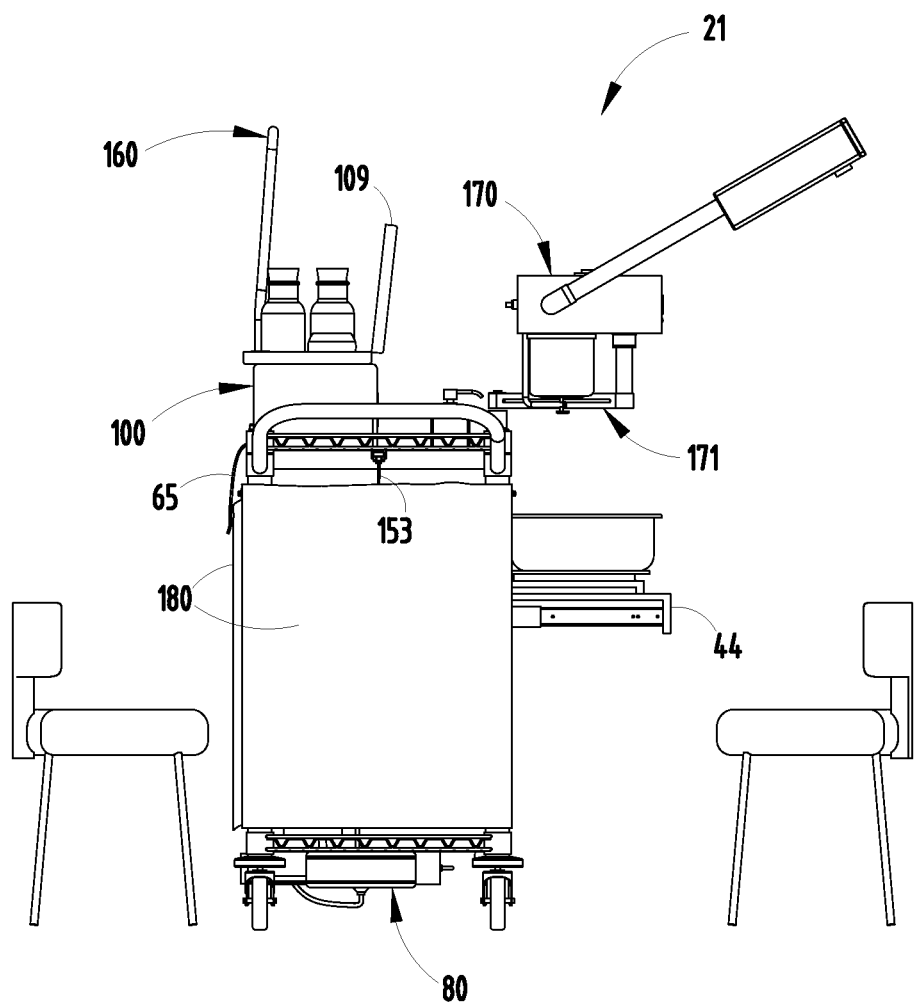
Figure 14:
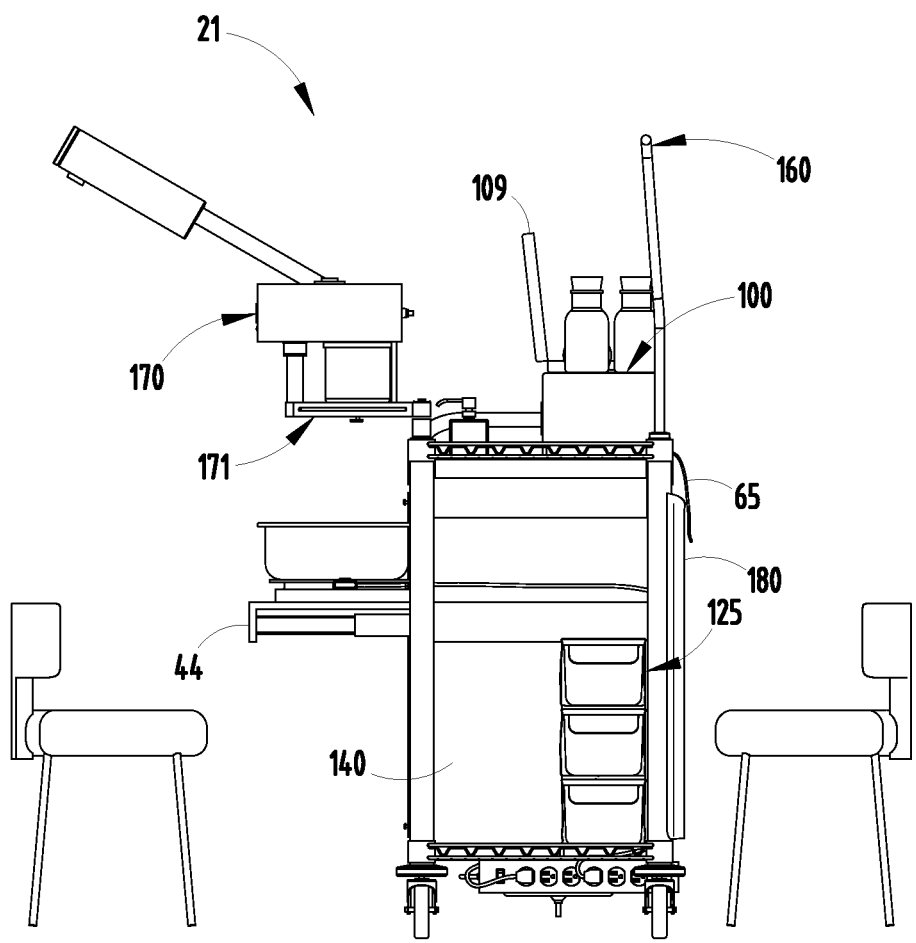

The middle laterally-extendable shelf 44 includes a panel (solid painted or powder coated top surface) that is supported by glides 45 on the glide-supporting post-to-post beam supports. A hot plate 130 is located on the drawer 44, and a plurality of different selectable tub modules (three such modules 131, 131A, 131B, 131C are illustrated in FIG. 8, but there could be many more such modules) are pre-assembled at the "home" location of the spa cart 21, so that a technician can selected tubs with product supporting the spa activities pre-selected by a client. For example, tub modules can be filled with hot stones 133, massage oils 134, aromas for aroma therapy, and the like. A switch 89' provides for automatic shut-off of the hot plate 130 upon closing the drawer 44 to a storage position. The bottom of the hot plate is lined with Vulcan cloth material which provides an impervious heat barrier to everything below.

The bottom support/shelf 28 (FIG. 8) supports the hot towel cabbie 140, which includes an insulated cabinet 141 and magnetically-latched door 142. Moist warmed towels 143 or other product can be stored in the cabinet 141 and kept warm, either being heated when placed therein and/or heated while in the cabinet 141.

A pedicure pan/tub 150 (FIG. 8) is stored in a zip-open fabric carrier 151 having a logo thereon. A top handle 152 on the carrier 151 engages a hook 153 on cart 21 located under cart handle 58. The dimensions of the tub, carrier 151, and handle 152 provide for compact positioning against the cart 21 when stored thereon under the cart's handle. A tub shelf 154 is provided to support a client's foot during treatment. Notably, the tub 150 can be used in many different ways, such as for soaking and other treatments.

Figure 15:
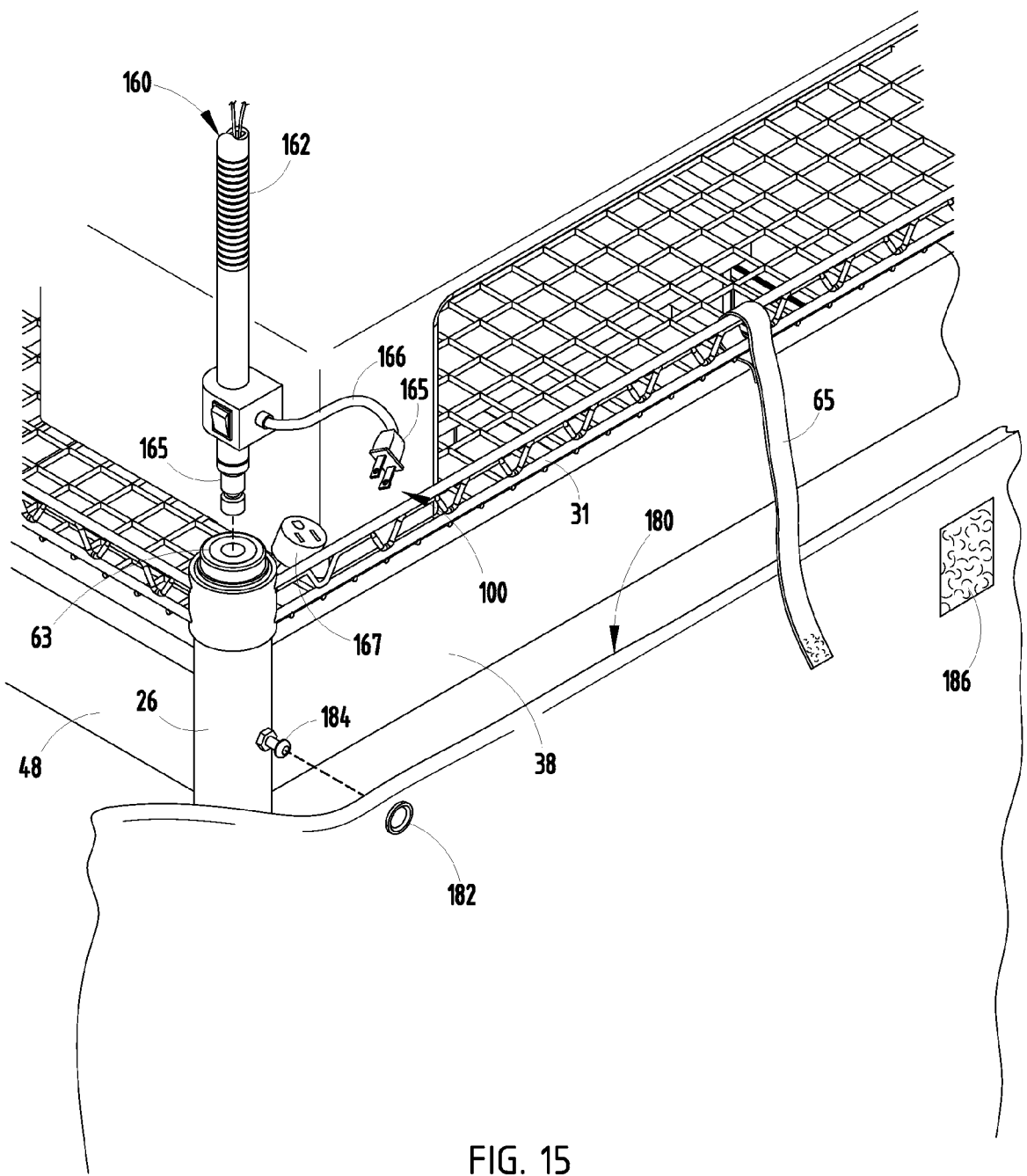
FIG. 15 is a fragmentary perspective view of a bottom of the post light with male post connector friction fitting into a female connector at a top of a corner post of the spa cart, and including the ring connector on the wrap for engaging the headed post connector part way down on the cart corner post.
Figure 16:
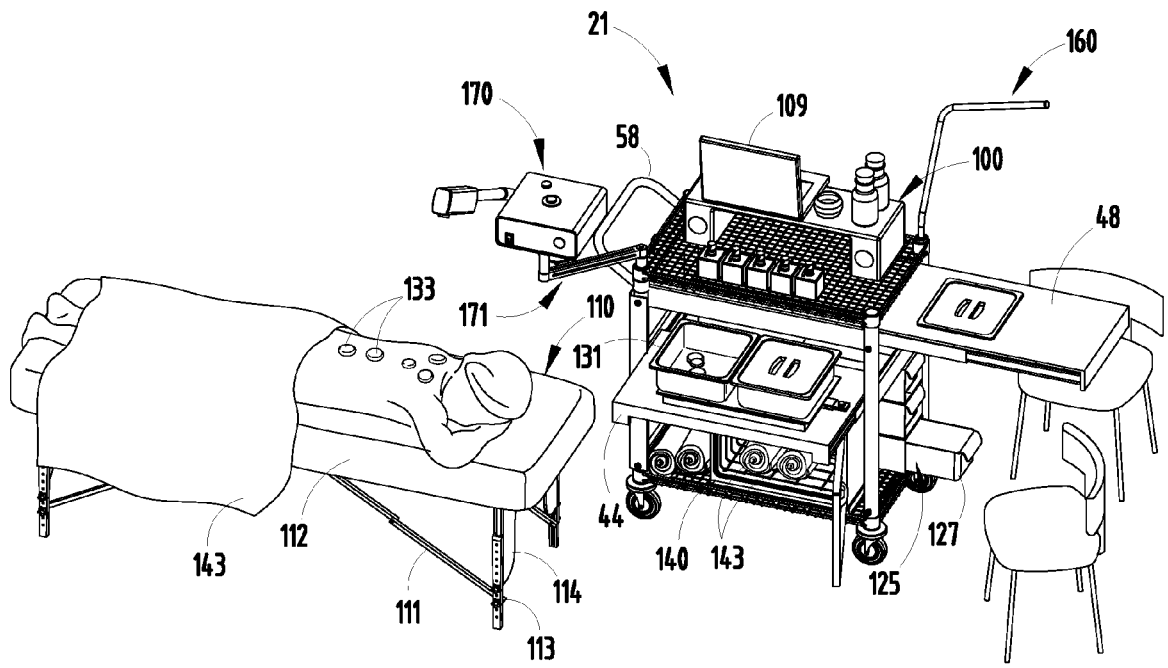
FIG. 16 is perspective view showing the spa cart opened and ready for use, the massage bed being opened and supporting a client undergoing stone therapy.
Figure 17:
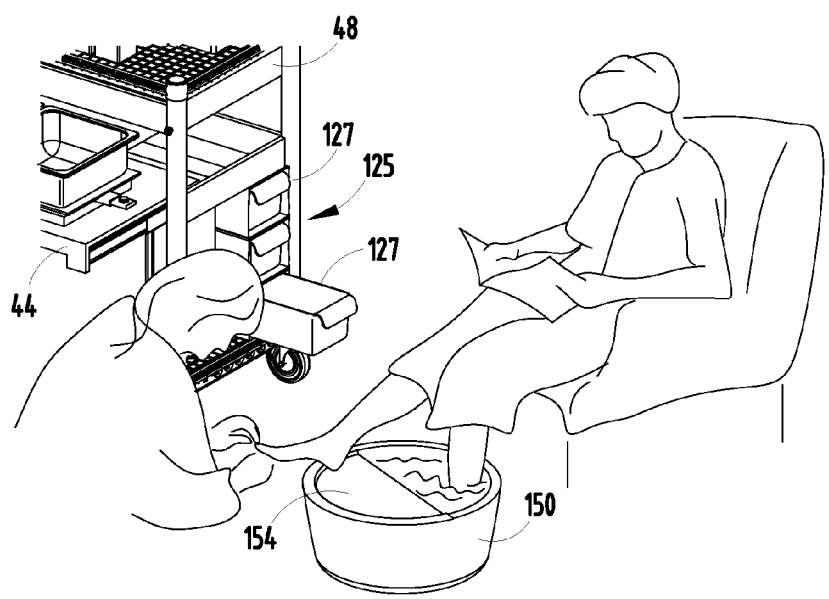
FIG. 17 is perspective view showing the spa cart opened and ready for use, the client receiving a pedicure.

A light can be supported on a corner post of the cart 21 for adjustable positioning as needed for the massage treatment, manicure, pedicure, etc. The illustrated light is an adjustable snake light 160 (FIG. 7) with two flexible snake sections 161, 162 and a rigid post tube section 163 and elongated light 164. A bottom stud connector 165 extends from the light and is configured to frictionally rotatably engage the female socket connector 63 on a top of the cart's post. Thus, the light 164 can be rotated and/or bent/manipulated to various positions over or cantilevered away from the cart 21, such as to position it over the cart 21 or extended over the manicure table or over the massage table. The light includes an electrical cord plug 166 (FIG. 15) that plugs into an extension cord 167 extending from the associated corner post, and is capable of spinning/rotating 360 degrees, and further can be located at any corner of the cart 21. Typically, the light will be positioned at the corner adjacent the technician's location when giving a manicure. Notably, the illustrated snake light could be replaced with a different light, such as a cantilevered/counterweighted boom-arm light and/or magnifier light and/or double-pivot cantilevered arm like is shown with steamer. Also, the electrical plugs can be similar to those plugs used on computers, in order to prevent components from being removed and used elsewhere.

The steamer/vapor unit 170 is a product known in the art, such that its details need not be described for an understanding by persons skilled in the art. The illustrated vapor unit 170 is capable of providing moist air and/or heated steam-filled air. It is supported by a double-pivot cantilevered arm 171, which includes a stud connector 172 rotatably engaging the socket of an associated top-of-post socket connector 63. The steam-generating unit 174 includes adjustable controls on its body, and an angularly adjustable dispenser arm 175 that is rotatable about its base support and also rotatable about its longitudinal axis. Its electrical plug 176 can be plugged in at an associated corner post.

The wraps (FIG. 8) include a three-side wrap/cover 180 and a single-side wrap/cover 190.

The illustrated covers 180/190 are made of vinyl, leather, and/or fabric 181. The cover 180 (and cover 190) includes top and bottom ring-shaped corner retainers 182,183 at both ends and also top ring-shaped corner retainers 182/183 at "inside" corners. The illustrated corner retainers 182 and 183 are metal rings configured to releasably engage headed studs 184, 185 on the associated corner posts at top and bottom locations at each corner. Mating Velcro® patches 186, 186' are located on the cover 180 to hold a single panel (i.e., one side section) of the wrap 180 open. This allows the remaining part of the three-side cover 180 to continue to cover unused sides of the cart 21. A logo 187 can be located on the wraps 180/190. The covers 180 and 190 are flat, which allows them to be cleanly folded for clean/attractive folded storage off to side when removed.

To operate the cart system, an operator initially pulls the cart's electrical extension cord from under the cart and plugs it into a room VAC outlet after entering the room. A usual next step is for the technician to take off the massage table that is attached through a Velcro loop off of the back of the cart, and then slide the table-supporting (ankle-height) shelf that it is attached to the back into its storage position. The technician then opens up the massage table at an appropriate location relative to the cart, and otherwise sets it up as desired (e.g., using optional head rests removably attached under the massage table's cushioned top). The illustrated massage table includes opposing halves that are unfolded to a co-planar condition, which causes table legs to expand to supporting positions. Sheets and linens are then put on the massage table after being retrieved from a tucked location inside the cart. Thereafter, the technician prepares whatever spa component/ apparatus that is going to be used. (Notably, the cart is initially stocked with modules having appropriate components and materials for supporting a particular spa activity, such as a tray holding hot stones, or paraffin materials, or moist towels and wraps for a body treatment). Notably, the cart is set up in a certain place relative to the massage table so that compartments/drawers on the cart are accessible to the technician for whatever service that they are going to do, because they often will be drawing not only product but also using spa components on the apparatus as part of providing the spa services.

For example, supported on a bottom shelf of the cart is a hot tray with a hot towel cabbie thereon. The hot towels are retrieved and used according to a known protocol. Notably, the moist hot towels are hot when placed on the cart at is original "home" location so that the client does not have to wait for the towels to heat up. The hot towel cabbie is always turned on at the time of service so that they remain plenty warm enough for use on the guest.

Supposing that the technician is going to do a massage, the typical steps are as follows. Notably, the massage does not necessary require the hot drawer, but the therapist will have had the table out and extended and fully dressed up with all of the linens. The massages will be performed and the use of hot towels then is often used to not only help to wipe off the oils but also to provide a service to the client giving further relaxation. If the guest wishes to have anything upgraded, there is a transaction table on top of the SweetSpa cart (including a computer, register, or the like) which can be used to record the transaction, including scheduling a next appointment. The illustrated cart uses a virtual system, which allows instant checking of schedules by the technician to make sure that they haven't been booked by someone else in the process. Also, upgrade can be made on the spot by the client into different/additional spa services. For example, hot stones are a popular upgrade for massages. Notably, during the massage or other spa activity, the equipment on the cart is always within reach, such as the steamer/vapor device, the infrared heater, a lamp (for illumination or treatment). When giving a massage, the technician provides services mostly by feel, however the various spa equipment can provide assistance where additional energy or vision or treatment (heat, moisture, etc) is required.

Spa activities such as facials, manicures, and pedicures require good lighting. In such case, the post light can be manipulated to provide directed additional light as necessary for providing an optimal service. It is contemplated that a variety of different lighting supports can be used, such as an articulating counterbalanced arm, a snake-like arm that is bendable in all directions in all sections along its length, and others. The illustrated light has two different snake-like bending sections connecting rigid tube sections, plus it rotates on the post support socket so you can orient that light in any direction and in a cantilevered fashion outside or over the cart or massage table.

If a client is having a manicure, the massage table does not necessarily have to be pulled off unless multiple services are being provided. In other words, the massage table could actually remain on the cart since various storage locations on the cart are accessible even when the massage table is left attached to the cart. For example, a single-side covering and a three-side covering is attached around the cart to cover its four sides. The flap on the right end of the cart can be pulled back and Velcroed open to keep it nice and neat and away from the manicure table. Next, the double sided pulled tray is pulled and extended to a partial or fully extended position. The tray includes a flat top surface positioned at a height suitable for a client to rest their hands on the tray while sitting in a chair. Concurrently, the technician is also sitting in a chair on an opposite side of the tray, in a location where the technician's hands are perfectly positioned to provide the manicure spa activity. Notably, the technician as seated is positioned adjacent a corner of the cart in a location where fingernail product and hand treatment products can be easily grasp while continuing to hold and work on the client's hands. Notably, the tray extends to about double its length, which provides an extra large working surface for the technician, such as an extended surface that is about 22 to 24 inches wide (in a direction away from the cart) and about 13-14 inches laterally (in a direction between the client and technician) and about 28-30 inches (or more preferably 29 inches) high. The illustrated tray includes roller-ball-bearing drawer glides that attach securely to the cart and that provide exceptional stability to the tray even when fully extended. For example, the client may lean on the tray and/or rest their hands on a towel and/or support product being applied, such that the tray requires sufficient strength. The post light can be adjusted and moved over very nicely so even when the room is darkened to create a spa atmosphere, the technician can still see the client's nails and fingers perfectly. Notably, none of the hotel's furnishings are used except for just seats in the room or space where the spa cart is located for business. For example, a nice cozy chair can be brought up next to the tray, with the technician sitting on the other side from the client. The technician, from their seated position, can draw out hot towels from a stored heated location in the cart if they wish, or grasp hot stones, or product for providing a paraffin treatment from the hot tray on the cart. Everything is literally very accessible immediately to the left (or right) of the technician (depending on where they are seated). Further, the products are well organized, at a reachable and ergonomically accessible height.

Notably, the height and shape of the tray and its supporting structure allow it to receive (i.e., match up to) almost every single chair that we, the inventors, have ever pulled up to it. Underneath the tray on the cart is also something that we have designed into. Basically it is a well organized area, which is important because there are so many implements needed for manicures and pedicures. The storage area includes various trays with product that are located underneath the pull-out tray that the technician can access as needed. For example, in the location immediately left of the technician, there is considerable space on the cart or on the pulled-out shelf or on one of the shelves under the cart's top shelf nail polishes and orange wood sticks and files are all kept. They are semi-hidden from view for aesthetics, but well arranged so that they are not simply in a cluttered visually-unappealing pile. Plus, their separation and clean arrangement leads to improved sanitary standards, which helps during state inspections that are conducted to make sure that everything is nice and clean.

The pedicure activity requires use of a bowl (or basin) that is attached to the cart under its handle. The bowl is accessed by unhooking its carrier/bag from the cart hook/Velcro® attachment, and then removing the bowl from the carrier. The guest is made comfortable in the coziest chair possible in their hotel room and the bowl is taken to the bath room and filled up with some warm sudsy water. Often, organic bath salts and/or herbs are put in to the bowl for aesthetics and ambiance. The guest places their feet into the water, where they are able to experience the pedicure right in their own room. When it is done, all of the water contents are dumped. Since it's all organic, the material can be simply dumped down a commode. The basin in then cleaned out and put it back on the cart, for transport with the cart out the door. Notably, other spa services may use the basin, such as where product is applied, such as muds, paraffins, hot stones, and/or hot/moist towels, each of which are accessed right from the cart.

As noted, the technicians can select appropriate modules for the cart at their originating location, (sometimes called a "Suite Spa™ station") depending on the requirements of a particular job. By having several different basins or modules that are already to select and go, they can quickly load up and go, depending on what the required service is. For example, they just take the tub modules (131) and replace it to where it needs to be in the room where spa services are being given, all hot and ready to go in the room.

Notably, 75-80% of the services will likely include massage therapy, and perhaps manicures and pedicures also being a higher usage, with many of the additional services being seasonal and location specific. Many of the specialty services like the herbal body wraps, hot stones, and mud therapies are more of an elite type of service often added onto the massage. Nonetheless, the present spa cart system allows a technician to quickly gather the spa components and products necessary for a particular location, and to transport them and later use them in an efficient and productive manner, while maintaining aesthetics, quality, and providing an excellent spa experience.

Facials require the set up of the massage table, so just as a technician would do when preparing for massage therapy, the massage table would be fully extended, and fully dressed up with its linens. The lamp would also be important as well as the steamer/vapor producing unit. These items are supported by male protruding connectors that extend into female sockets positioned inside a top of one or more of the corner tubes making up the cart frame. These items are also supported by an articulating arm or cantilevered arm extending from the protruding connectors. The illustrated post light includes a bottom male protruding connector that rotates in its mating male socket connector, and further includes two snake-like sections bendable in multiple directions, with an elongated light on its end. It is noted that the light apparatus could also include a magnifier (not illustrated) if desired. The steamer is supported by a two-pivot cantilevered support arm, which can be manipulated to position the steamer over the massage table (i.e., away from the cart, while still supported on the cart), or can be positioned over the pulled out tray (e.g., during a manicure or hand treatment). The illustrated multi-bending arm can position the steamer as much as 3 feet away from the cart and over the face of a client. Thus, steam can be directed right towards the face while the technician is taking out hot towels, hot stones, or paraffins, whatever they need for the facial. The illustrated arm is a double pivot cantilevered arm that basically has a post that goes down into the top of the corner post of the main frame of the cart. Notably, any of the four corner posts of the cart frame could be the host for supporting any of the light, the steamer, the infrared light, or other apparatus (such as a microdermabrasion apparatus). Significantly, while the technician is doing the manicure at one end, the steamer is out of the way at an opposite corner. Further, the technician can work with the client concerning colors, products, and otherwise interact with the guest for an optimal experience. The illustrated steamer and cantilevered arm allow the steamer to be stored tight against the transaction counter so that it is out of the way but also so that the overall aesthetic makes the stored arrangement logical and "seem to fit." Notably, the entire spa experience is supported entirely by products and components off the cart and supported by selected modules as needed, allowing the technician to do virtually every and any type of facial that the client wants right from the cart.

Hot stone therapy uses the massage table. The technician applies oils or whatever product is needed to the client, the products being retrieved from the cart from easily accessible locations, making the transition of retrieval to application relatively smooth and uninterrupted. Typically, the hot stone treatment starts with a little bit of a massage and then hot stones are incorporated as an extension of the technician's hand. The hot stones stay nice and warm for a long time, allowing the stones to provide an extended therapy via the heat from the stone to soften muscle tissues.

Depending on what modules, product, water/moisture and towels, spa-equipment, and/or massage table are placed on the cart (and also what electrical components, transaction counter, computer and the like are on the cart), a fully loaded cart can weigh up to about 210-220 pounds. Nonetheless, the present fully loaded cart (including the massage table) will fit through a doorway as small as 30 inches or even 29 inches wide. Notably, with the massage table removed, the cart will fit through a door that is only about 20 inches. The handle and front fixed-axis wheels and rear steerable wheels provide a smooth stable cart that can be controllably moved by a person of only 100 pounds or so, since they can lean into the cart and also provide leverage as needed due to the wide handle. It is preferable that the wheels be lockable so that the cart can be locked in a fixed position during use, and also preferable that the wheels include a rubber or soft tread so that the cart rolls along with minimal noise and clatter. The existing wheels are about 4 inches in diameter, which provides a good feel and ability to roll over bumps or entranceways and thresholds.

The cover (also called a wrap) is made from a high quality vinyl or fabric or leather sheeting or multi-layer sheeting, preferably with the hotel logo and information thereon. The cover is made up by a one-side cover and a three-side cover, with a top and bottom ring at each corner. Each ring is continued to engage a mating protruding top and bottom finger connector on each corner post. Hook-and-loop material, such as Velcro® is used to hold back one section of the three-side cover when only one side of the cart needs to be accessed. When removed, the cover(s) can be folded and placed to one side. Their folded appearance maintains the high quality feel of the spa experience, and their low weight and easy removal/re-attachment eliminate them as a distraction.

The cart includes a frame including a cross-wire mesh bottom stabilizer, a cross-wire mesh top stabilizer, and intermediate supporting structure that supports the three pull out trays, each connected at four corners by corner posts. An electrical cord is supported on a retractable reel under the bottom stabilizer along with a multi-electrical-outlet surge protector. The various electrical spa-supporting components, such as the steamer and the light include electrical cords that extend vertically through the posts and radially out through a post sidewall into engagement with one of the electrical outlets. The top stabilizer includes a tempered glass top surface and includes a perimeter railing to keep displayed product from falling off of the top surface. Glass also covers the pull out trays and the bottom shelf, especially the pullout tray for the manicure since manicure products often include solutions that etch or damage other materials. The tempered glass is pretty indestructible to any type of nail finishings or removers so the glass works really well for this cart.

In back of the hot towel cabbie/warmer, there is a three-drawer soft cabinet that is small enough to fit behind the cabbie yet vertically high enough to support three drawers/tubs filled with product. For example, each drawer/tub can be filled with different colors of fingernail polish and/or other material (a selectable module). Each drawer/tub is accessible an end of the cart to the right of the hot towel cabbie, and is clear or translucent so that its contents can be seen even before retrieval.

A herbal blanket is an extension of massage therapy, and includes a good-sized herbal sheet soaked in appropriate conditioning materials to form a herbal blanket. The blanket is folded in such a way that when the technician pulls it out, it unfolds perfectly to cocoon a client. The blanket is, for example, steeped in hot tea or in other kinds of detoxing herbals. It is another one of those modules that you can grab and dip in and away you go.

The illustrated modules include, for example, a hot stone tray, a herbal-holding tray, a paraffin holding tray. However, there are many additional modules that can be constructed/assembled, such as for different manicure, pedicure, facial mud, herbal, and other treatments. For example, it is contemplated that a microdermabrasion electrical spa component can be mounted to one of the corner posts, plugged in, and made operational very quickly.

A mud treatment basically requires that the technician bring out one serving of mud at a time, such as in a little metal serving cup. The cup can be heated either in the hot towel cabbie or on the hot plate or can be pre-heated and made ready to go.

A hair-removing treatment, such as a wax, can be provided in a module and used for eyebrows or legs.

A paraffin dip can be used on ones hands. The paraffin treatment forces moisture back into the enzymes in ones hands, kind of like when someone puts their finger in a candle and it coats it. A paraffin hand is first lotioned up, and then the hands are dipped in and then taken out. The paraffin material pulls right off almost like a glove.

Another component is an infrared lamp or sensor that could be set on one of the corner posts to either adjacent the handle or at the other end.

Each of these are wonderful ways of being able to help detox the body and keep the body nice and warm during certain services. Further, each of them are supported on the cart for portable and efficient use, yet providing a luxurious environment and spa experience.

The steamer has its own supply of water in it. It is supported on a cantilevered arm that rotates on a corner post of the cart, and includes a multi-bend cantilevered arm permitting optimal positioning.

Music is an important part of the whole spa experience provided by the present cart system. When the cart is brought into a room, the technician backs up a little bit and takes the massage table off, setting it up in an adjacent location to the cart. The electrical cord of the cart is plugged in to the room electrical power to provide electrical power to the cart's spa components and equipment. The first thing that the technician does is go to a notebook where there is stored a good library of spa music that they can just press on and play the spa music. Notably, the music can be provided through a computer instead of an iPod device. Further, the system can be wireless or wired or stored on a memory device on the cart, such as via an iPod music storage device. The illustrated cart has an iPod docking station for an iPod player. There are speakers built into vertical side supports of the transaction station/table which are connected to the iPod docking station for powering the system. It gives a wonderful sound throughout the whole entire room causing the hotel room to actually turn into like a spa treatment room. The illustrated side supports are hollow and tend to amplify the sound from the speakers, further providing an excellent spa experience.

It is contemplated that additional upgrades can be added to the present cart system. For example, additional drawers could be added as an upgrade to the standard cart next to the hot towel cabbie. Some drawers would be underneath the towel cabbie for storage of additional products or washcloths or whatever. They would potentially be built right into the cart as well.

The cart can include various power-supplying outlets, including hard wired outlets, outlets provided by extension cords, and the like. It is preferable that at least one electrical outlet provide full time power, such as for powering a computer or iPod.

The present cart can be easily upgraded such as by providing novel finishes or wraps. For example, the wrap could include gold plating or platinum plating or silk or tapestry. Individual wraps could be provided for individual different equipment, such as for different microdermabrasion machines or facial equipment. Such items would be compact and would fit very well on this cart as an option on the cart for the original purchasing entity.

Depending on a hotels finishes and themes, we can adapt the cart to match it from fabrics to woods to hard surfaces, whether it be granite, glass, gem stones, you name it we could incorporate that on the finishes wherever you see grid work or the wrap itself and we have already been doing that right along with the different hotels we have been in.

It is to be understood that variations and modifications can be made on the aforementioned structure without departing from the concepts of the present invention, and further it is to be understood that such concepts are intended to be covered by the following claims unless these claims by their language expressly state otherwise.

The embodiments of the invention in which an exclusive property or privilege is claimed are defined as follows:

1. A spa cart system comprising:
a wheeled spa cart with at least one component configured to support at least one spa service selected from a group of spa services including a back massage, a body massage, a facial, stone therapy, manicure, pedicure, microdermabrasion treatment, paraffin treatment, tanning, and a spa therapy activity using hot moist towels, the cart defining a longitudinal centerline and having a retractable support supported on glides that is movable transversely to the longitudinal centerline between an extended use position and a retracted storage position; and
a massage bed with cushions and that is releasably supported on the retractable support and secured by a top retainer to a side of the wheeled spa cart.

2. The system defined in claim 1, wherein the top retainer includes at least one mechanical fastener.

3. The system defined in claim 2, wherein the fastener includes a strap.

4. The system defined in claim 1, wherein the spa cart includes a push handle, and the bed hangs on a side of the spa cart with a portion of the bed generally adjacent the push handle.

5. The system defined in claim 1, wherein the massage bed includes a folding bed frame.

6. The system defined in claim 1, wherein the spa cart and massage bed combined have a total width less than 30 inches, so that the combined spa cart and massage bed fit through a standardized hotel doorway.

7. The system defined in claim 1, wherein the at least one component includes at least one electrical component for providing the spa service, the at least one electrical component being selected from a group including a light on a flexible post support mounted to the cart for easy positioning; a vapor generating unit for a facial; a heated container storage for heating product such as stones, moist towels, paraffin product; a heating plate for heating product placed thereon; a music system including a music player and speakers.

8. The system defined in claim 1, wherein the spa cart includes a top surface with edge flange for storing spa products thereon for display.

9. The system defined in claim 1, wherein the spa cart includes a pull-out manicure station having a flat top surface at a height suitable for a manicure service for a seated client.

10. The system defined in claim 9, wherein the manicure station includes glides supporting a pull-out shelf capable of being pulled out a distance greater than half a length of the cart.

11. The system defined in claim 1, wherein the spa cart includes a pull-out lower shelf support for supporting the massage bed.

12. The system defined in claim 1, wherein the at least one component includes a manicure station, and the spa cart includes a pull-out shelf on a side adjacent the manicure station.

13. The system defined in claim 1, wherein the spa cart includes a push handle, and includes a pull out shelf with hot plate thereon and further includes modules on the hot plate.

14. The system defined in claim 1, wherein the spa cart includes a transaction counter supported on one side of and above a top surface of the cart.

15. A spa cart system comprising:
a wheeled spa cart with corner posts and multiple extendable shelves supported by glides on the corner posts and having at least two open sides and two open ends for accessing the shelves, the corner posts each having top and bottom headed studs, the glides defining at least two different shelf-extension directions; and
at least two flexible sheet wraps covering the open sides and the two open ends, the at least two flexible sheet wraps being releasably attached to the top and bottom headed studs on the corner posts, including two of the at least two flexible sheets using a same one of the top and bottom headed studs, whereby stored product is selectively accessible from anyone of the open sides and the open ends.

16. The system defined in claim 15, wherein the shelves include at least two shelves at different levels and that are extendable in two different directions.

17. The system defined in claim 15, wherein at least one of the shelves is supported on double-length extendable glides.

18. The system defined in claim 15, wherein the at least two wraps includes a three-sided wrap and a one-sided wrap, the one-sided wrap including ends that overlap with the three-sided wrap when on the cart.

19. The system defined in claim 15, wherein the at least two wraps include ring-shaped fasteners for engaging mating headed posts on the cart.

20. The system defined in claim 15, wherein the cart includes a flap-holding fastener to hold a portion of at least one of the two flexible wraps open for unencumbered access to the cart while a portion of another of the at least two wraps is still attached to the cart.

* * * * *